United States Patent
Olson

(10) Patent No.: US 11,219,552 B2
(45) Date of Patent: Jan. 11, 2022

(54) INTRAOCULAR FILTER DEVICE AND METHODS OF USING SAME

(71) Applicant: The Regents of the University of Colorado, a body corporate, Denver, CO (US)

(72) Inventor: Jeffrey Olson, Denver, CO (US)

(73) Assignee: THE REGENTS OF THE UNIVERSITY OF COLORADO, A BODY CORPORATE, Denver, CO (US)

( * ) Notice: Subject to any disclaimer, the term of this patent is extended or adjusted under 35 U.S.C. 154(b) by 478 days.

(21) Appl. No.: 16/186,030

(22) Filed: Nov. 9, 2018

(65) Prior Publication Data
US 2019/0151147 A1  May 23, 2019

Related U.S. Application Data

(63) Continuation-in-part of application No. 14/916,659, filed as application No. PCT/US2014/054531 on Sep. 8, 2014, now Pat. No. 10,518,002.
(Continued)

(51) Int. Cl.
*A61F 9/00* (2006.01)
*A61K 9/00* (2006.01)
(Continued)

(52) U.S. Cl.
CPC .......... *A61F 9/0017* (2013.01); *A61K 9/0051* (2013.01); *A61L 27/50* (2013.01);
(Continued)

(58) Field of Classification Search
CPC .. A61F 9/0017; A61F 2/16; A61F 2250/0067; A61L 27/50; A61L 2300/432; A61L 2300/404; A61L 2300/252; A61L 2430/16; A61L 2400/12; A61L 27/16; A61L 27/12
See application file for complete search history.

(56) References Cited

U.S. PATENT DOCUMENTS

2002/0026176 A1  2/2002  Varner
2005/0004663 A1  1/2005  Llanos
(Continued)

FOREIGN PATENT DOCUMENTS

WO    2006110487       10/2006
WO    2012/149468 A2 * 11/2012
(Continued)

OTHER PUBLICATIONS

USPTO; Non-Final Office Action dated Mar. 8, 2019 in U.S. Appl. No. 14/619,659.
(Continued)

*Primary Examiner* — Carlos A Azpuru
(74) *Attorney, Agent, or Firm* — Snell & Wilmer L.L.P.

(57) ABSTRACT

An implantable device comprising a substrate capable of capturing an intraocular target molecule and to methods of use thereof. The substrate may be capable of capturing a target molecule present in the eye and/or from fluid of the eye (e.g., an intraocular target molecule). In some embodiments, the substrate has a relatively high affinity for a target molecule.

18 Claims, 18 Drawing Sheets

Related U.S. Application Data

(60) Provisional application No. 61/874,759, filed on Sep. 6, 2013.

(51) Int. Cl.
*A61L 27/50* (2006.01)
*A61F 2/16* (2006.01)
*A61L 27/44* (2006.01)

(52) U.S. Cl.
CPC ......... *A61F 2/16* (2013.01); *A61F 2250/0067* (2013.01); *A61L 27/44* (2013.01); *A61L 2300/252* (2013.01); *A61L 2300/404* (2013.01); *A61L 2300/432* (2013.01); *A61L 2300/604* (2013.01); *A61L 2430/16* (2013.01)

(56) References Cited

U.S. PATENT DOCUMENTS

| | | |
|---|---|---|
| 2006/0110428 A1 | 5/2006 | deJuan |
| 2006/0235367 A1 | 10/2006 | Takashima |
| 2007/0150058 A1 | 6/2007 | Shahinpoor |
| 2008/0147021 A1 | 6/2008 | Jani |
| 2008/0269318 A1 | 10/2008 | Romano |
| 2010/0034864 A1 | 2/2010 | Spedden et al. |
| 2011/0098640 A1 | 4/2011 | Horne |
| 2011/0117169 A1 | 5/2011 | Sanford et al. |

FOREIGN PATENT DOCUMENTS

| | | |
|---|---|---|
| WO | 2012149468 | 11/2012 |
| WO | 2013003620 | 1/2013 |
| WO | 2015035296 A2 | 3/2015 |

OTHER PUBLICATIONS

USPTO; Notice of Allowance dated Aug. 22, 2019 in U.S. Appl. No. 14/916,659.

Notice of Allowance dated Jul. 1, 2021 in U.S. Appl. No. 16/705,989.

International Searching Authority, Notification of Transmittal of The International Search Report and the Written Opinion of the International Searching Authority dated Feb. 19, 2015 in Application No. PCT/US2014/054531.

Notification of International Preliminary Report on Patentability dated Mar. 17, 2016 in Application No. PCT/US2014/054531.

USPTO, Restriction Requirement/Election dated Oct. 14, 2016 in U.S. Appl. No. 14/916,659.

USPTO, Non Final Office Action dated Aug. 7, 2017 in U.S. Appl. No. 14/916,659.

USPTO, Restriction Requirement/Election dated Feb. 16, 2018 in U.S. Appl. No. 14/916,659.

USPTO, Final Office Action dated Aug. 27, 2018 in U.S. Appl. No. 14/916,659.

Katschke et al. Inhibiting Alternative Pathway Complement Activation By Targeting The Factor D Exosite. Jan. 2012.

Guilliams. Free Radicals, Antioxidants and Eye Diseases. Not as Incurable as We Once Thought. 1999.

Gasche et al. Complement Deplection During Haemofiltration with Polyacrilonitrile membranes. 1996.

Extended European Search Report dated May 15, 2017 in European Application No. 14842818.8.

\* cited by examiner

INTRAOCULAR FILTER DEVICE AND METHODS OF USING SAME

CROSS-REFERENCE TO RELATED APPLICATIONS

This application is a continuation-in-part of U.S. application Ser. No. 14/916,659, filed Mar. 4, 2016, which is a U.S. 371 National Stage Application of PCT Application No. PCT/US2014/054531, filed Sep. 8, 2014, which claims priority to U.S. provisional patent application Ser. No. 61/874,759, filed on Sep. 6, 2013, the entire contents of which are incorporated herein by reference in their entirety.

BACKGROUND

Many ocular disorders are caused by or associated with one or more proteins; some such proteins are vasoactive compounds like vascular endothelial growth factor (VEGF), complement factors, and inflammatory factors. Current treatments typically attempt to decrease levels and effects of VEGF. Studies have shown that existing treatments are costly and rely on repeat injections. Further, endogenous proteins may be associated with progressive retinal degeneration, such as non-exudative macular degeneration. A need exists for improved treatments for ocular disorders, and particularly long-term treatment regimens that do not require repeat intraocular injections.

SUMMARY

In various embodiments, the present disclosure provides an implantable device comprising a substrate capable of capturing a target molecule present intraocularly (e.g., an intraocular target molecule). In some embodiments, the device is capable of being regenerated in situ.

In various embodiments, the present disclosure provides an implantable device comprising a substrate comprising one or more of hydroxyapatite and a ceramic (e.g., a bioceramic), and a captured angiogenic compound.

In various embodiments, the present disclosure provides a method of treating an ocular disorder in a subject, the method comprising implanting into an eye of the subject a device comprising a substrate capable of capturing a target molecule present in the eye or in fluid of the eye (e.g., an intraocular target molecule); and capturing the target molecule from the eye or from fluid of the eye. In some embodiments, the device is implanted into the eye such that the device extends into the vitreous cavity and/or the anterior chamber of the eye. In some embodiments, the method further comprises, after capturing the target molecule from the eye or from fluid of the eye, regenerating the device in situ. In some embodiments, the method further comprises, after the step of regenerating the device in situ, capturing the target molecule from the eye and/or from fluid of the eye. In another embodiment, fluid from the eye may be shunted outside the eye. For example and without limitation, fluid may be shunted from the eye using a glaucoma shunting device or similar apparatus. In one embodiment, a filtering device as described herein may be placed in the reservoir of the shunting device to remove angiogenic proteins from the fluid before the fluid is returned to the eye.

The forgoing features and elements may be combined in various combinations without exclusivity, unless expressly indicated herein otherwise. These features and elements as well as the operation of the disclosed embodiments will become more apparent in light of the following description and accompanying drawings.

BRIEF DESCRIPTION OF THE DRAWINGS

FIG. 6A and FIG. 6B depict a configuration in which the blinking of a subject with the LPP facilitates tear flow from inside a hollow lumen reservoir back to the surface of the eye, according to various embodiments.

Figure 1:
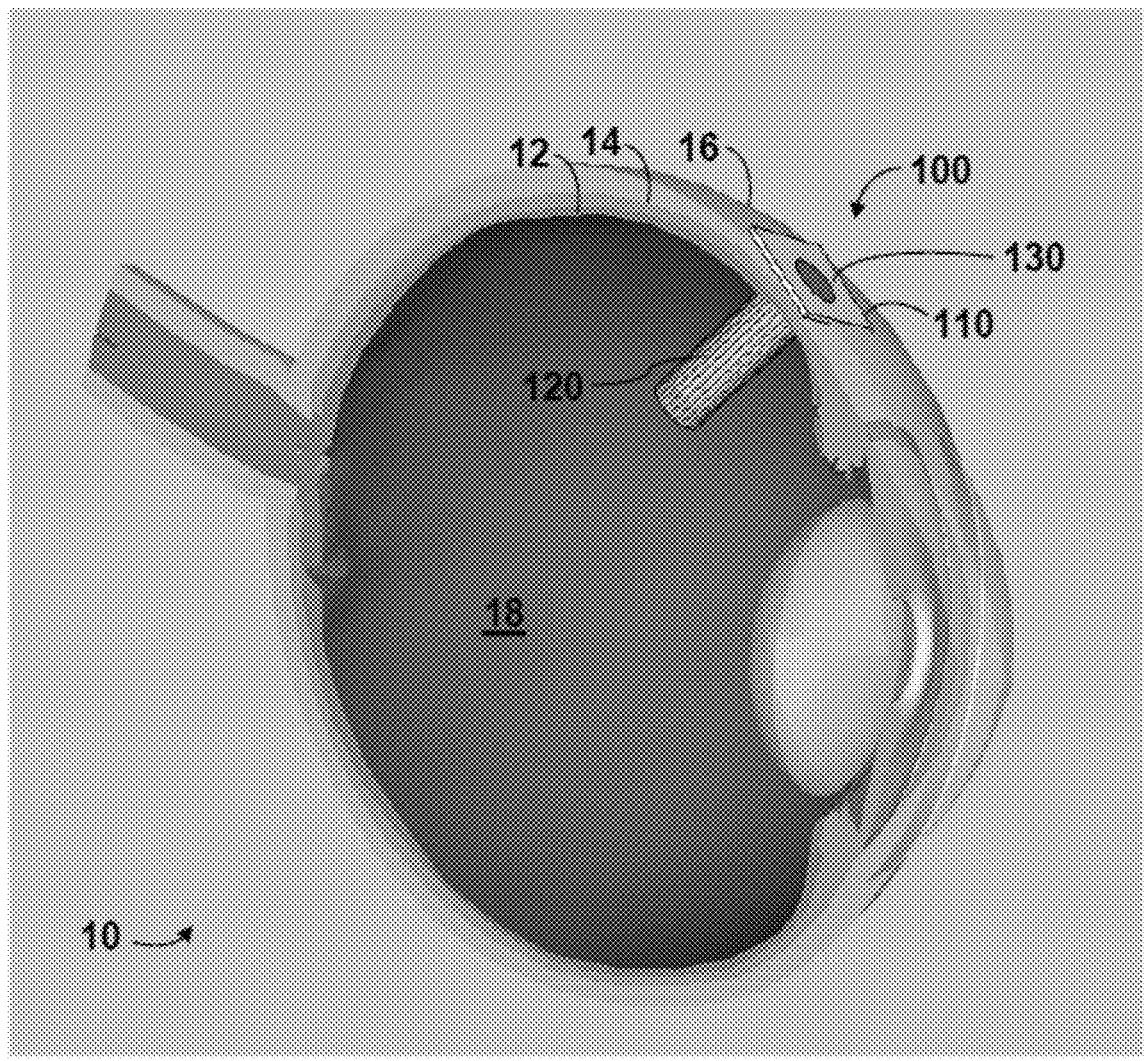
FIG. 1 depicts a device of the present disclosure implanted in an eye of a subject, according to various embodiments.

The subject matter of the present disclosure is particularly pointed out and distinctly claimed in the concluding portion of the specification. A more complete understanding of the present disclosure, however, may best be obtained by referring to the detailed description and claims when considered in connection with the drawing figures.

DETAILED DESCRIPTION

While the present invention is capable of being embodied in various forms, the description below of several embodiments is made with the understanding that the present disclosure is to be considered as an exemplification of the invention, and is not intended to limit the invention to the specific embodiments illustrated. Headings are provided for convenience only and are not to be construed to limit the invention in any manner. Embodiments illustrated under any heading may be combined with embodiments illustrated under any other heading.

The use of numerical values in the various quantitative values specified in this application, unless expressly indicated otherwise, are stated as approximations as though the minimum and maximum values within the stated ranges were both preceded by the word "about." Also, the disclosure of ranges is intended as a continuous range including every value between the minimum and maximum values recited as well as any ranges that can be formed by such values. Also disclosed herein are any and all ratios (and ranges of any such ratios) that can be formed by dividing a disclosed numeric value into any other disclosed numeric value. Accordingly, the skilled person will appreciate that many such ratios, ranges, and ranges of ratios can be unambiguously derived from the numerical values presented herein and in all instances such ratios, ranges, and ranges of ratios represent various embodiments of the present invention.

The term "treatment" in relation a given disease or disorder, includes, but is not limited to, inhibiting the disease or disorder, for example, arresting the development of the disease or disorder; relieving the disease or disorder, for example, causing regression of the disease or disorder; or relieving a condition caused by or resulting from the disease or disorder, for example, relieving, preventing or treating symptoms of the disease or disorder. The term "prevention" in relation to a given disease or disorder means: preventing the onset of disease development if none had occurred, preventing the disease or disorder from occurring in a subject that may be predisposed to the disorder or disease but has not yet been diagnosed as having the disorder or disease, and/or preventing further disease/disorder development if already present.

In one embodiment, the present disclosure provides a method of treatment of an ocular disorder comprising implanting a device according to the present disclosure in an eye of a subject. The term "ocular disorder" herein refers to any disease or disorder of the eye or related tissues (i.e. retina, macula, retinal blood vessels, etc.) or any symptom thereof. Non-limiting examples of ocular disorders include macular degeneration (e.g., exudative and non-exudative age-related macular degeneration), bull's eye maculopathy, cataract, central serous retinopathy, chorioretinal scars, chorioretinitis, chorioretinitis from toxoplasma, chorioretinitis from tuberculous, choroid, choroidal (central areolar, choroidal atrophy, choroidal degeneration, choroidal detachment, choroidal haemorrhage, choroidal haemorrhage and rupture, choroidal neovascularization, choroidal sclerosis, choroideremia, choroiditis, cystoid macular edema, detachment of retinal pigment epithelium, diabetic retinopathy, dystrophy, epiretinal membrane, generalized, gyrate atrophy, glaucoma, Harada's disease, hereditary choroidal dystrophy, diabetic macular edema, cystoid macular edema, hereditary retinal dystrophy, hypertensive retinopathy, macula scars of posterior pole (postinflammatory or posttraumatic), macular edema, or peripapillary, pars planitis, papillitis, peripheral retinal degeneration, posterior cyclitis, retinal detachment, retinal haemorrhage, retinal neovascularization, retinal vascular occlusions, retinitis, retinitis, retinitis, retinitis pigmentosa, retinochoroiditis, retinochoroiditis, retinochoroiditis, retinopathy, retinopathy of prematurity, retinoschisis, separation of retinal layers, solar retinopathy, syphilitic chorioretinitis, infectious and non-infectious uveitis, retinal artery occlusion, retinal vein occlusion, retinal and choroidal angiogenesis or neovascularization, retinal and choroidal ischemia, and other ocular events. In other embodiments, the device described herein could be used in connection with treating sinusitis or arthritis, or more generally, any ailment commonly associated an inflammatory response and/or any of the target molecules described herein.

In one embodiment, the present disclosure provides an implantable device comprising a substrate capable of capturing a target molecule present in the eye and/or from at least one of a vitreous humour and an aqueous humour of an eye (e.g., an intraocular target molecule). In some embodiments, the substrate has a relatively high affinity for a target molecule. In some embodiments, the substrate has a relatively high affinity for an angiogenic compound. In some embodiments, the substrate has a higher affinity for an angiogenic compound (e.g., VEGF) than for a VEGF antagonist such as ranibizumab, bevacizumab or pegaptanib.

Vascular endothelial growth factor (VEGF) is a protein that promotes vasculogenesis and angiogenesis, and is known to mediate retinal neovascularization. Overexpression (among other factors) can therefore lead to ocular disorders such as macular degeneration or age-related macular degeneration. In some embodiments, the target molecule is a protein. In some embodiments, the target molecule is an angiogenic compound, such as VEGF. In some embodiments, the angiogenic compound comprises a human isoform of VEGF, such as one or more of $VEG_{121}$, $VEGF_{121}b$, $VEGF_{145}$, $VEGF_{165}$, $VEGF_{165}$, $VEGF_{165}b$, $VEGF_{189}$, or $VEGF_{206}$. In some embodiments, the target molecule is adversely associated with retinal physiology, such as PEDF. In other embodiments, the target molecule is selected from:

Bone morphogenetic protein-2 (BMP2), Hypoxia-inducible factor-1α. (HIF-1 α), P2X2, Taurine, Advance glycation end products, Claudin-5, Occludin and JAM-A, microRNAs, RhoJ Pathway, Caveolin-1 (Cav-1), Apelin-13, Exendin-4 and GLP-1, Vascular adhesion protein-1, Angiopoietin-like protein 4 (ANGPTL4), IL-6, IL-8, CXCR3, (CCL2?), MMP-2, 7, and/or 9, TIMP (MMP inhibitors) 1, 2, and/or 3, Cathepsins D, Cystatins, High Temperature required factor A (HtrA) 4, HtrA1 SNP rs11200638, Urokinase-type plasminogen activator, Tissue-type plasminogen activator, IL-6, IL-8, and/or IL-17, IL-2 and TNFa, Pigment epithelium derived growth factor, Placental growth factor, Fibroblast growth factor, Heat shock proteins (HSP27), Human factor H-related protein 2-(CFHR2), IGF-1 and IGFBP-2, INFgamma and TNFa, Norrin, Neural cell adhesion molecule (N-CAM), Erythropoietin (EPO) and IGF-1, Angiopoietin-1, IL-B, Nox and RAAS, Apelin/APJ system, 15-lipoxygenase-1 (15-LOX-1), Prolactine and vasoinhibins, TNF, MCP-1, MCP-2, any molecule involved in the complement cascade (e.g., Complement Factor D, C3, C5, C3a, C5a), interleukin-1, oxygen free radicals, apolipoproteins, lipofuscin, and/or inflammatory proteins or those of an infectious etiology.

In some embodiments, the present disclosure provides an implantable device comprising a substrate comprising one or more of hydroxyapatite and a ceramic, and a captured angiogenic compound. In some embodiments, the device is capable of releasing the captured angiogenic compound (and/or modified angiogenic compounds, degradation products of the angiogenic compound, etc.) after denaturation of at least a portion of the captured angiogenic compound, for example by exposure to a laser. In some embodiments, the device is capable of capturing an additional amount of the angiogenic compound after exposure to the laser. In some embodiments, the angiogenic compound comprises VEGF (e.g., a human isoform of VEGF) from vitreous fluid of a subject.

Generally, substrates suitable for use in a device consistent with this disclosure have large surface areas and high affinities for an angiogenic compound, such as VEGF, or other proteins associated with ocular disease. In some embodiments, the substrate comprises hydroxyapatite, a ceramic (e.g., a bioceramic), tricalcium phosphate, bioglass, glass, bone, calcium phosphate, metallic alloys, a membrane or a combination thereof. As used herein, the term "hydroxyapatite" refers to a mineral having a formula $Ca_{10}(PO_4)_6(OH)_2$. In some embodiments, the substrate comprises, consists essentially of, or consists of hydroxyapatite. In some embodiments, the substrate comprises, consists essentially of, or consists of a ceramic such as mesoporous hydroxyapatite (MHA). In some embodiments, the substrate does not include a polyethylene glycol-conjugated oligonucleotide. In some embodiments, the substrate comprises, consists essentially of, or consists of polyacrylonitrile (PAN), PAN polymers, carbon nanotubes, polysulfone, chitosan, biomedical polymers, polystyrene, polyvinyl chloride, poly(D. L-lactide), polymethyl methacrylate (PMMA), and poly(2-hydroxyethyl methacrylate)PHEMA, acrylic, silicone, dextran, bisacrylamide, alkyl chains, agarose, polyacrylamide, silica, nanoparticles, shape memory polymers, alumina, silicon, graphite, grapheme, gold. DMPC, phospholipid membranes, collagen, and/or glycosaminoglycan, among other materials that are capable of dialyzing protein or molecular moieties. In other embodiments, the substrate may be a shape memory polymer, plastic, acrylic, nylon, or a combination of various materials. In some embodiments, the substrate comprises, consists essentially of, or consists of a solid, a porous matrix, a gel, a sheet, a membrane, a colloid, a microparticle, or a nanoparticle. In some embodiments the substrate is durable. In other embodiments, the substrate is dissolvable and/or biodegradable. In some embodiments, the substrate comprises biodegradable pellets that can be injected intravitreally and that subsequently degrade or dissolve. In one embodiment, the device is coated with antibodies specific to a target protein, molecule, or moiety, including those belonging to inflammatory, angiogenic, or infectious etiologies.

In other embodiments, a PAN substrate may comprise, for example, fibrous PAN hydrogel formed from a combination of nitrile groups and hydrophilic groups. In some embodiments, the proportion of nitrile groups and hydrophilic groups can be changed to modify the physical properties of the device. Notably, PAN hydrogels have good biocompatibility, low toxicity, and high tear strength. In other embodiments, a PAN substrate may comprise, for example, a copolymer of acrylonitrile and sodium methallylsulfonate.

Figure 21:
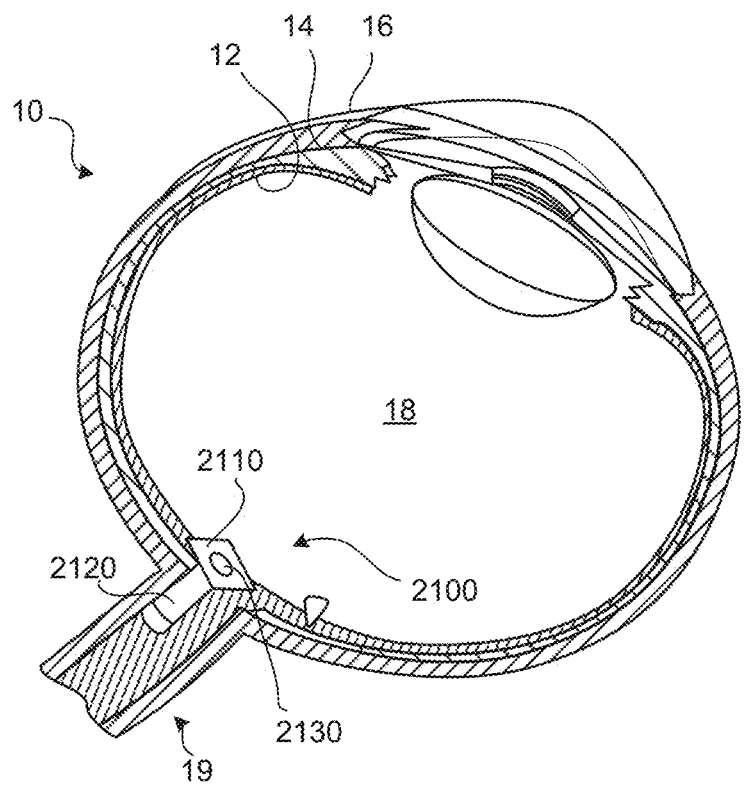
FIG. 21 illustrates an implantable device positioned in an optic nerve of the eye, according to various embodiments.

In some embodiments, such as the embodiment shown in FIG. 1, at least a portion of the implantable device 100 has a size and shape that imparts a relatively high surface area to the device. For example, in one embodiment device 100 comprises an anchoring portion 110 and the substrate may comprise an immersed or immersible portion 120, wherein the anchoring portion 110 is configured to be in contact with and secured at one or more tissues of the eye, and wherein immersed or immersible portion 120 is configured to be in contact with vitreous fluid 18. In some embodiments, the device 100 is implanted through (e.g., is in contact with) one or more of: the sclera 16, the choroid 14, and/or the retina 12. In various embodiments, and with momentary reference to FIG. 21, the implantable device 2100 may be positioned such that the immersible portion 2120 is disposed in the optic nerve 19 of the eye 10. While two different positions of the implantable device are shown in FIGS. 1 and 21, these two depictions do not represent exclusive locations where the implantable device can be installed. That is, the implantable device may be implemented in various orientations/positions within the eye, and may further be implemented in other, non-ocular applications, as described above.

In some embodiments, immersed or immersible portion 120 defines a size and shape different from that of an anchoring portion 110 of device 100. Immersed or immersible portion 120 of the device 100 may have a polygon shape, or a shape of a cylinder, sphere, partial sphere, cone, truncated cone, or a combination thereof. The device may also be composed of multiple hollow tubes, similar to dialysis tubing, which can be bundled together.

In some embodiments, the device 100 has an anchor portion 110 with which the device can be attached to a portion of the eye tissue, for example by suture. In some embodiments, the device 100 has an indicator portion 130 which may be used, for example, to provide a practitioner with information about the type of material(s) used in device 100. In other embodiments, indicator portion 130 may provide the practitioner a target zone or information about where a regenerating laser may be focused.

Figure 2:
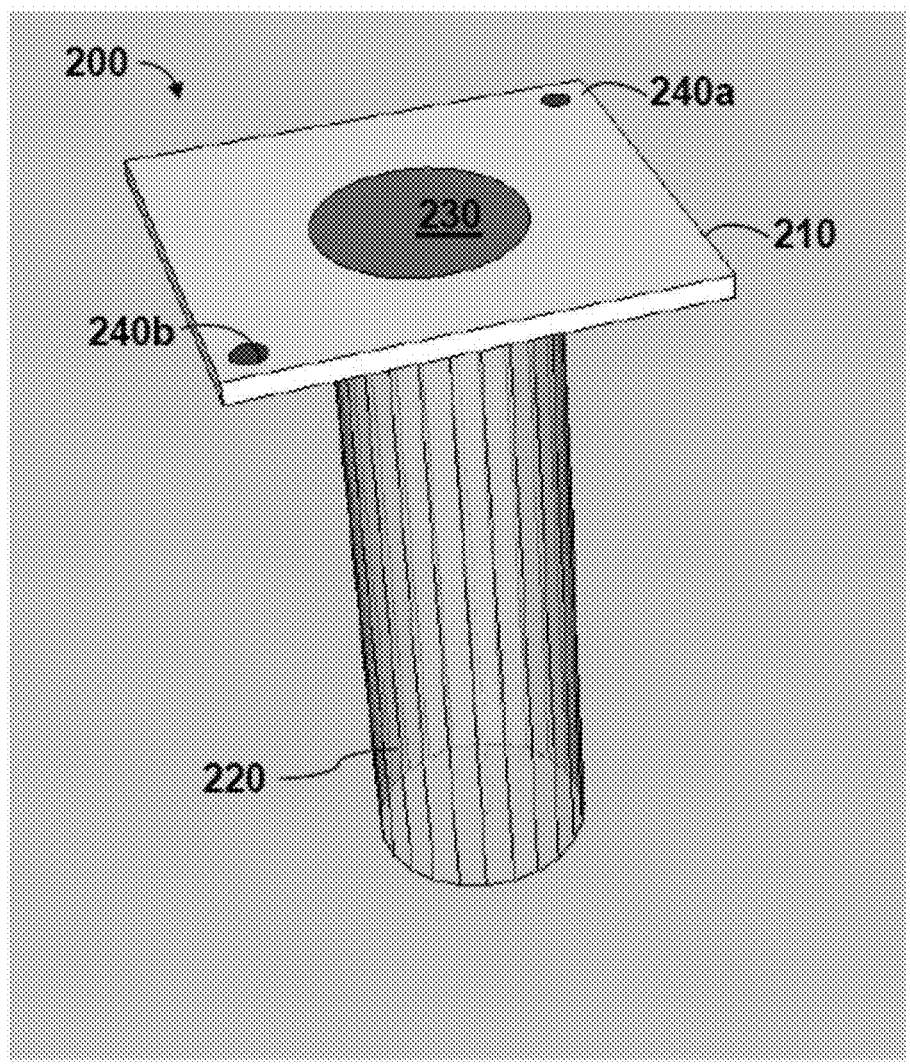
FIG. 2 depicts a portion of one embodiment of a device of the present disclosure having a generally cylindrical cross section, according to various embodiments.

In other embodiments, for example as shown in FIG. 2, an implantable ocular device 200 comprises an anchoring portion 210 and an immersed or immersible portion 220. In some embodiments, device 200 includes one or more anchoring features (240a, 240b) which allow a practitioner to secure device 200 to a tissue of the eye. For example, anchoring feature(s) 240a-b may comprise holes through which a suture can be passed. In some embodiments, the substrate may be incorporated into other implants which are commonly placed in the eye such as glaucoma drainage devices, aqueous shunting devices, and intraocular lenses, as described in greater detail below.

In some embodiments, immersed or immersible portion 220 of device 200, may have a generally cylindrical, tapered cylinder, or conical cross section. Further, it may be spherical, tubular, or in a sheet-like configuration. In some embodiments, device 200 has an indicator portion 230 which may be used, for example, to provide a practitioner with information about the type of material(s) used in device 200. In other embodiments, indicator portion 230 may provide the practitioner a target zone or information about where a regenerating laser may be focused (regeneration described in greater detail below). In some embodiments, indicator portion 230 is applied to or formed as part of anchoring portion 210. In some embodiments, indicator portion 230 is configured to allow a needle to pass therethrough, for example to allow removal, replacement, or exchange of materials inside immersed or immersible portion 220 without removing device 200 from the eye. In some embodiments, indicator portion 230 comprises a self-sealing material, for example to prevent fluid from passing therethrough after penetration by a needle. In various embodiments, the indicator portion 230 is a port defined in the anchoring portion 210, and the substrate, which may be contained within, may be embedded within, or may form part of the immersible portion 220, may be regenerated, removed, exchanged, and/or replaced via the port.

In some embodiments, the device comprises an implantable lacrimal punctal plug (LPP) including substrate material capable of controlling flow of lacrimal fluid and capturing a target molecule present in the eye or in fluid of the eye (e.g., an intraocular target molecule). In some embodiments, the LPP is placed in the lacrimal puncta of the eye, reducing or blocking tear flow out of the eye while substrate material traps target molecules of interest. An example of a suitable substrate and target molecule may include PAN substrate targeting Complement Factor D. Notably, the term "ocular dialysis" (e.g., "intraocular dialysis") may also be used to refer to the herein disclosed devices and methods of removing target molecules, such as anti-inflammatory proteins, by adsorption to a membrane or substrate.

Figures 6A, 6B:
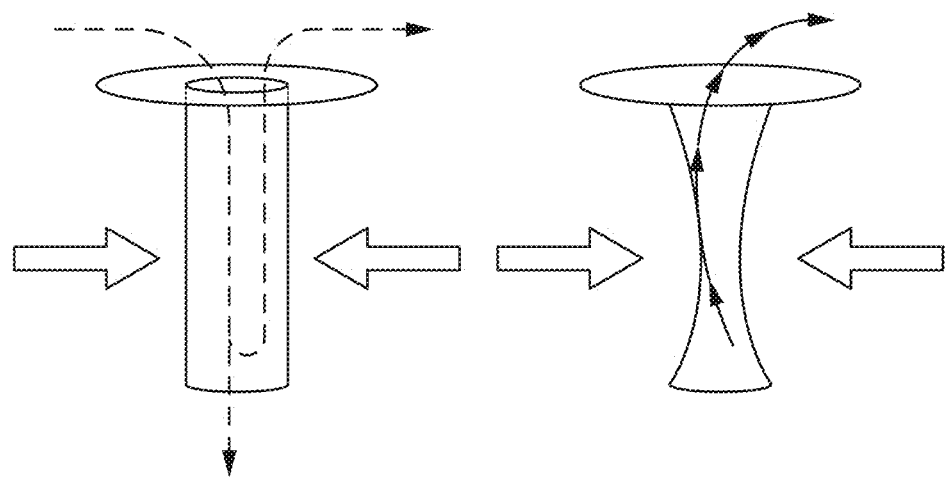
FIGS. 6A and 6B depict a lacrimal punctal plug (LPP) of the present disclosure having embedded substrate, compressible sides, and a hollow lumen, according to various embodiments. More specifically.

In some embodiments, and with reference to FIGS. 6A and 6B, a LPP may have a generally cylindrical cross section and a lumen comprised of a hollow tube, adsorptive material, or the like. In some embodiments, the sides of the lumen 621 are compressible. In some embodiments, and with reference again to FIG. 6, compression of the lumen 621, for example, by blinking of a subject with the LPP facilitates tear flow from inside a hollow lumen reservoir back to the surface of the eye. This configuration enables both the capturing of target protein molecules present in the eye and control of the flow of filtered fluid back to the surface of the eye. In this configuration, the presence of filtered, previously secreted tears is advantageous as a vehicle for rehydration of the eye and as a means of diluting inflammatory proteins of the eye.

The LPP can be removably inserted into the upper and/or lower punctal apertures or punctum of the eye. With momentary reference to FIG. 7, this insertion blocks the opening and the canaliculus communicating therewith, to prevent drainage of lacrimal fluid (tears). The LPP can be made of suitable materials, such as polymers comprised of PAN, a hydrophilic polymer, or alternate suitable substrates. In an example embodiment, the LPP of is made of or coated with PAN substrate that adsorbs target proteins, such as Complement Factor D. In other embodiments, the LPP could be configured to accommodate hydroxyapatite (HA)/VEGF binding as well.

Figure 7:
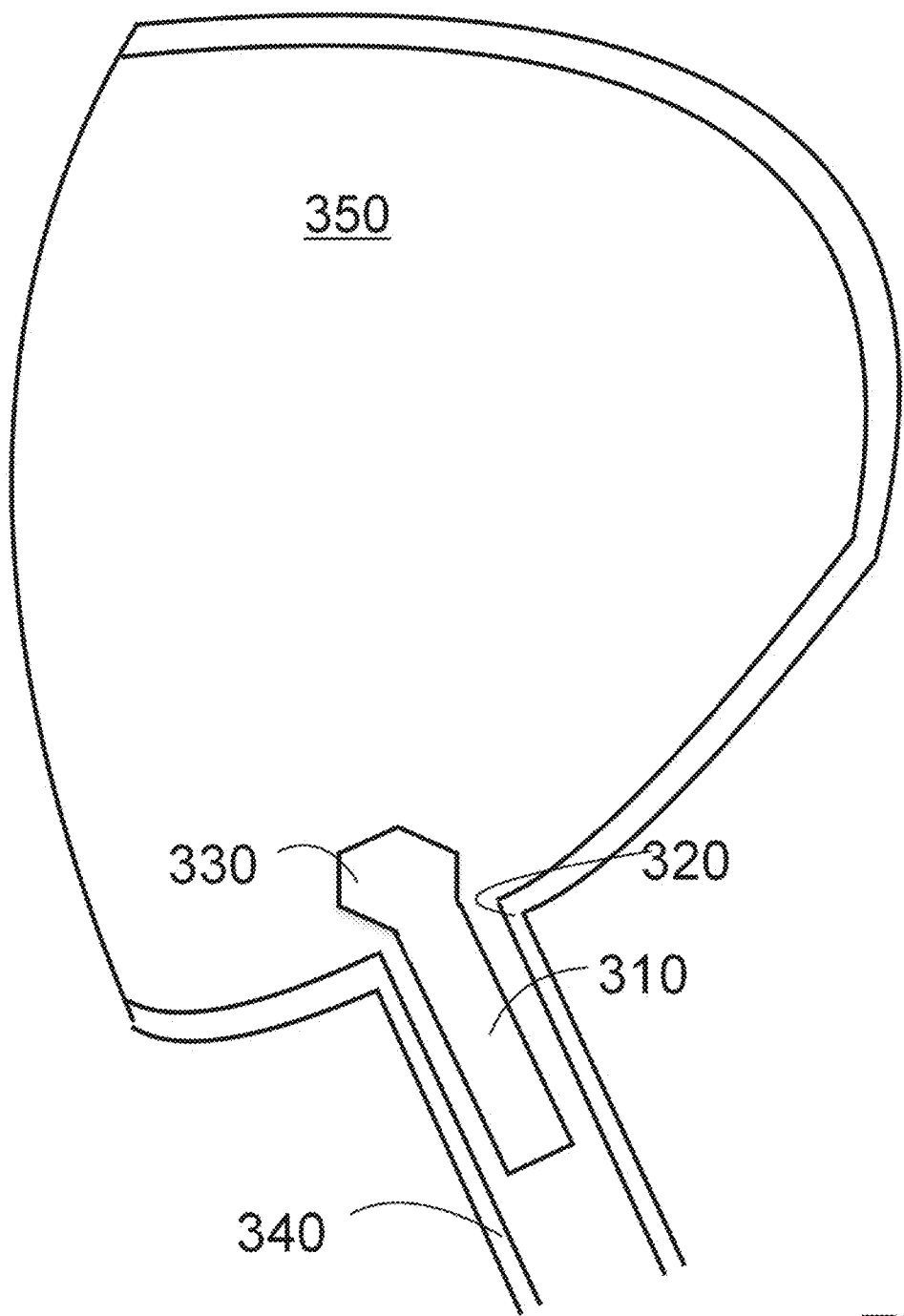
FIG. 7 depicts a portion of one embodiment of a LPP located in the punctal aperture of a subject, according to various embodiments.

In some embodiments, and with reference to FIG. 7, a LPP comprises a projection 310 which extends into the punctal aperture 320 of the eye 350, extending into the anterior chamber of the eye. The LPP comprises a plug 330 connected to the one end of the projection 310 for immobilization against the punctal aperture 320 and sealing the canaliculus 340 against the flow of tears onto the surface of the eye 350.

In some embodiments, a substrate, such as PAN, is mixed or embedded into the device in a homogenous fashion. In other embodiments, the substrate is embedded in a site-specific fashion, capable of modification based on the desired treatment. For example, if inflammation at the walls of the canaliculus is targeted, the substrate may be applied only to inner surfaces of the plug that are adapted to be in contact with or near the tissues of the canaliculus. The LPP embodiment described above may be particularly well-suited for placement in the punctum of the eye, but is not limited thereto and could be installed on or in other eye regions where convenient and useful.

In some embodiments, the implantable device comprises a subconjunctival implant (SI) including substrate material with an affinity for target molecules present in the eye and/or in fluid of the eye. Suitable substrate and target molecules may include, for example, PAN substrate and target protein such as Complement Factor D.

Figure 8:
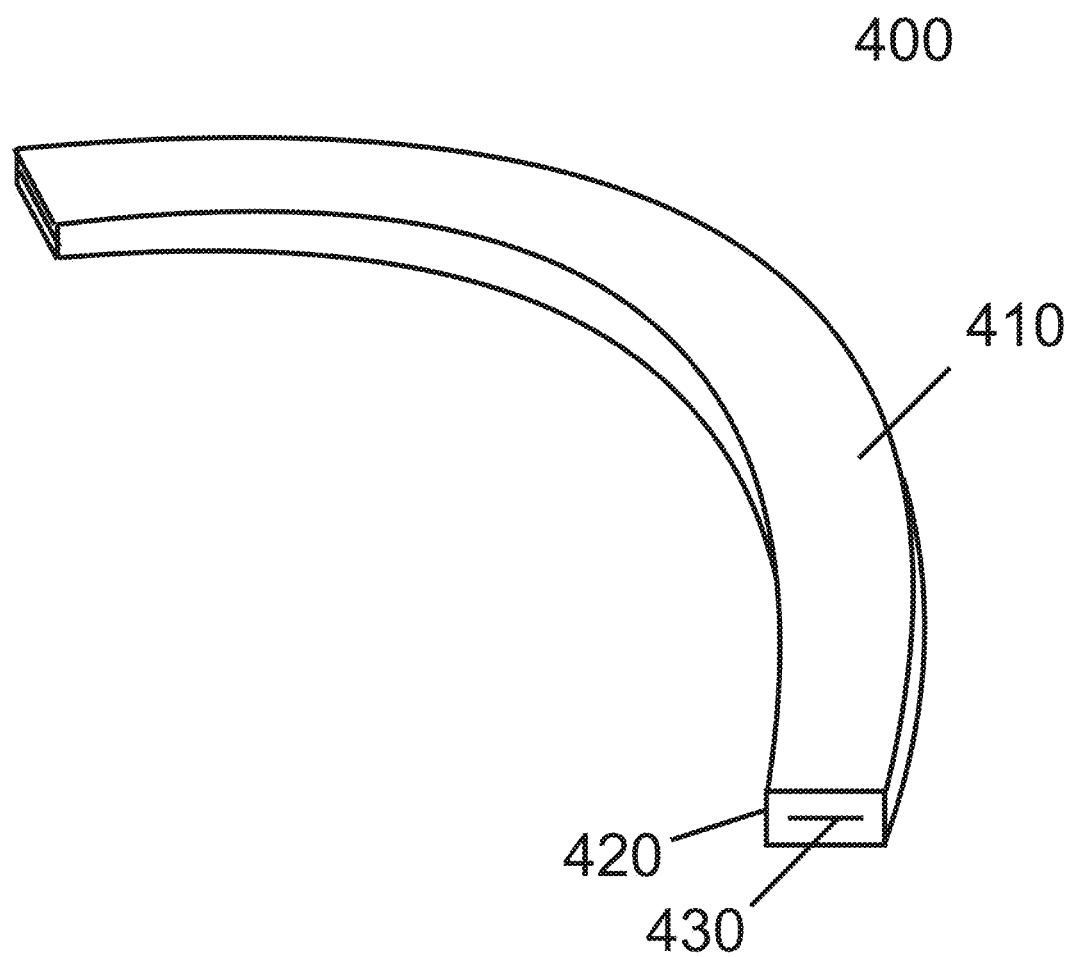
FIG. 8 depicts a portion of one embodiment of a subconjunctival implant (SI) having embedded substrate, according to various embodiments.

In some embodiments, and with reference to FIG. 8, an SI 400 comprises a body 410 which that may include an inner matrix 420 having a substrate 430 dispersed therethrough. The substrate, such as PAN, may be incorporated into a matrix of various solid materials. In embodiments, any solid material chemically compatible with the substrate agent can be used. In some embodiments, the implant may be a thin disc or wafer and may be placed behind or in front of the intraocular lens. In other embodiments, this implantable disc may be lasered, and then replaced if necessary.

In some embodiments, the implantable device may include a curved channel which follows the curvature of the retina or cornea and extends from the projection for draining fluid from the anterior chamber. In other embodiments, a valve portion may provide for venting of fluid from the vitreous chamber. In other embodiments, the SI device can be placed behind the surface epithelium within the subconjunctival space, avoiding invasive procedures that require piercing of the vitreous body. It also is possible to install these implants at or near other specific sites on or within the eye, such as intravitreal, if desired or useful.

In some embodiments, the SI device has a substrate covering a portion, or all, of the SI device surface. In some embodiments, PAN substrate, or the like, is applied to a well-defined portion of the SI device, such as only to the outer portion of the device. The SI embodiment described above may be particularly well-suited for subconjunctival or intravitreal placement, but is not limited thereto and could be installed on or in other eye regions where convenient and useful.

Figure 9A:
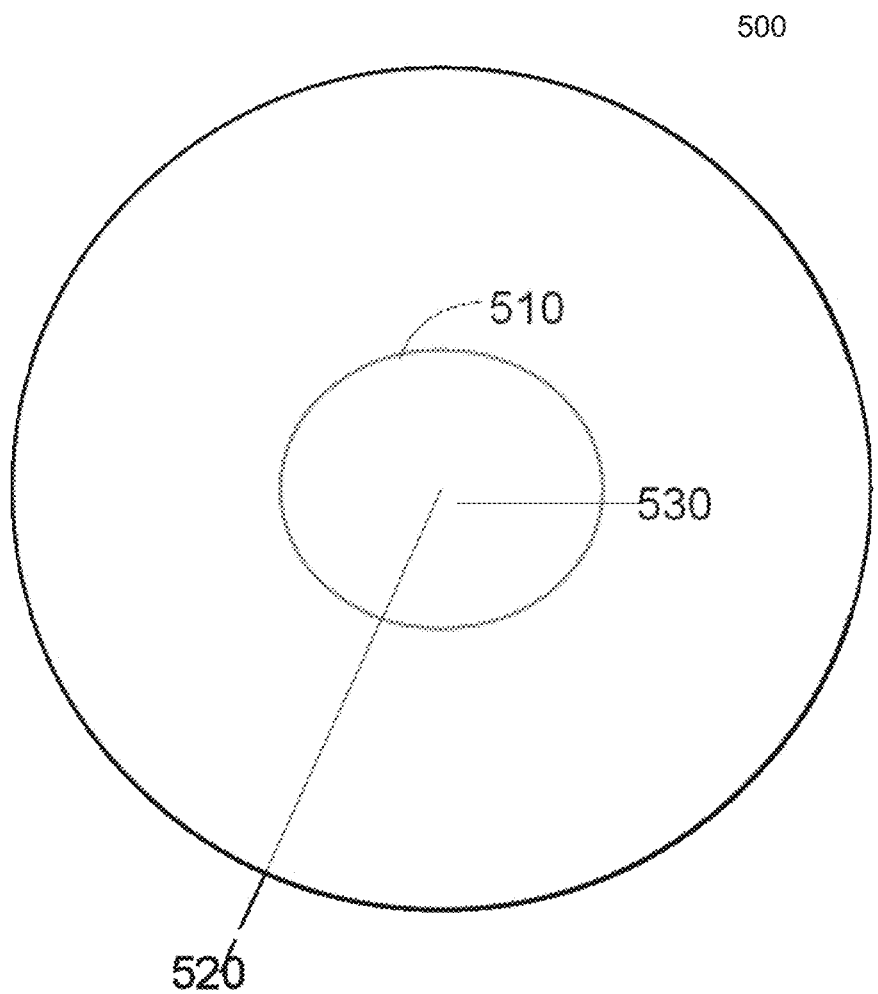
FIGS. 9A and 9B depict a portion of one embodiment of a lens, such as a contact lens (CL), having embedded substrate, according to various embodiments.
Figure 9B:
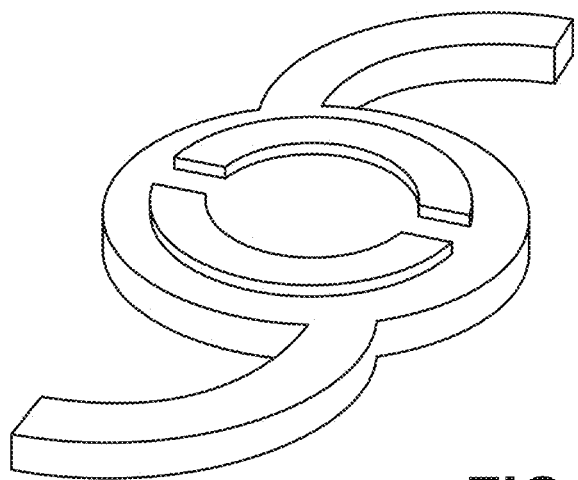

In some embodiments, and with reference to FIG. 9A, the implantable device comprises a contact lens (CL) including substrate material with an affinity for target molecules present in the eye and/or in fluid of the eye. Suitable substrate and target molecules may include, for example, PAN substrate and target protein such as Complement Factor D. In some embodiments, and with reference to FIG. 9A, a CL 500 has a shape that provides refractive correction. In an alternate embodiment, the CL has a shape that does not provide refractive correction. In other embodiments, the CL is a corneal lens 510 or a scleral lens.

In some embodiments, a method for forming a CL may comprise a step of applying a cross-linking treatment to a mat of polymer fibers forming the CL surface. In other embodiments, the method may comprising adding a substrate, such as PAN, to a polymer lens formulation either before the lens is formed or by soaking the formed CL in a solution containing the substrate. In various embodiments, the substrate 560 may be integrated into an intraocular lens 555. In some embodiments, the substrate is applied only to, or comprises only, a portion of the CL. For example, PAN substrate may be applied only to, or comprise only, an annular ring in the CL, in alternating rings, or to the outer ring 520 of the CL. In other embodiments, the substrate may be applied only to, or comprise only, the center 530 of the CL, a slice of the CL, or an otherwise well-defined pattern of the CL. The CL embodiment described above may be particularly well-suited for placement at the surface of the eye, but is not limited thereto and could be installed on or in other eye regions where convenient and useful.

Figure 10:
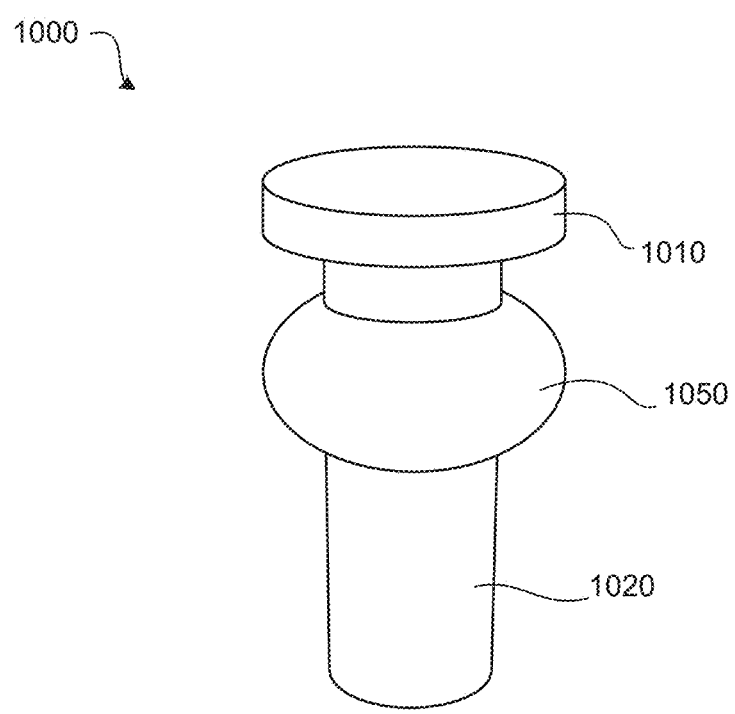
FIG. 10 illustrates an implantable device having an immersible portion that includes a bulbous ring, according to various embodiments.

In various embodiments, the immersible portion of the implantable device may include a retention feature configured to prevent inadvertent extraction of the implantable device from the eye. In various embodiments, and with reference to FIG. 10, the implantable device 1000 may include a retention feature 1050 that serves as a second flange to help retain the implantable device 1000 in place and prevent extraction of the device. That is, the implantable device 1000 may be inserted into tissue such that a section of tissue is disposed between the anchoring portion 1010 and the retention feature 1050. For example, the implantable device 1000 may be a bulbous ring or other similar shape that extends circumferentially around the immersible portion 1020 (e.g., the bulbous ring may extend around a lumen that forms the immersible portion). The bulbous ring may be inflatable, thus allowing for the immersible portion 1020 to be easily inserted into tissue before the bulbous ring is inflated.

Figure 11:
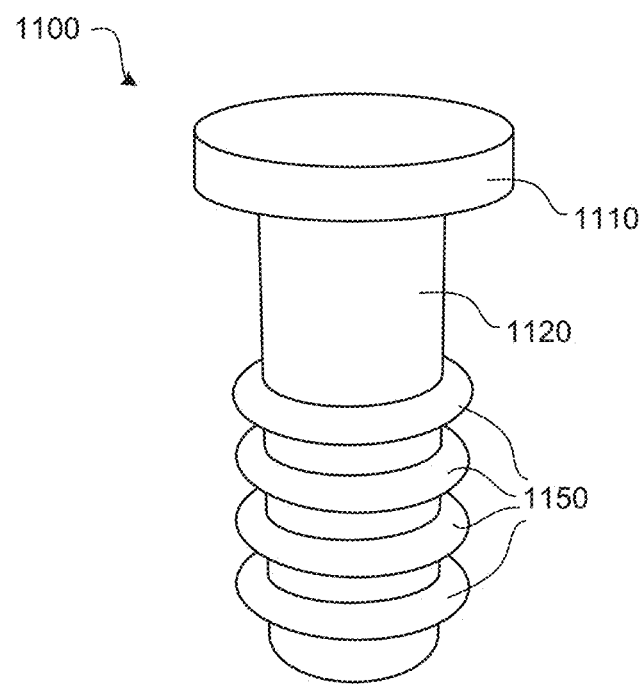
FIG. 11 illustrates an implantable device having an immersible portion that includes a plurality of ridges extending circumferentially around a lumen of the immersible portion, according to various embodiments.

In various embodiments, and with reference to FIG. 11, the implantable device 1100 includes retention features 1150 that have the form of one or more ridges that extend circumferentially around the immersible portion 1120. For example, the one or more rows of ridges 1150 may extend around a lumen that forms the immersible portion 1120. In various embodiments, the ridges 1150 may have a tapered bottom lip and an abrupt, step-wise top lip (e.g., the lip facing the anchoring portion 1110), thus facilitating insertion of the immersible portion 1120 while preventing extraction of the immersible portion 1120.

Figure 12:
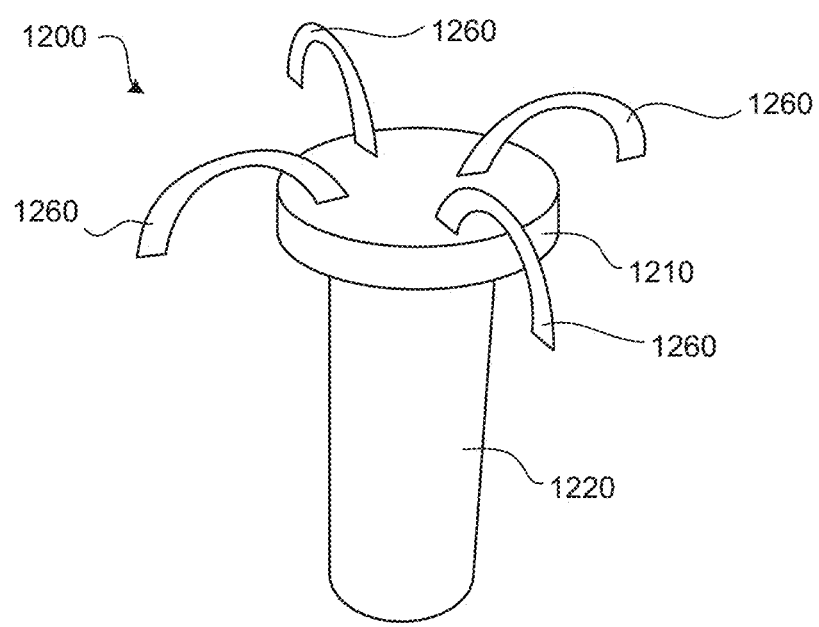
FIG. 12 illustrates an implantable device having an anchoring portion that includes a plurality of auxiliary retention features configured to prevent migration of the implantable device, according to various embodiments.

In various embodiments, and with reference to FIG. 12, the implantable device 1200 may include one or more auxiliary retention features 1260 that extend from the anchoring portion 1210 (instead of from the immersible portion 1220). That is, the auxiliary retention features 1260 may be features the are configured to prevent, or at least mitigate, migration of the implantable device 1200. For example, the one or more auxiliary retention features 1260 may include arms that extend radially outward from the anchoring portion 1210. These arms may prevent or at least mitigate unwanted extraction, rotation, and/or other types of movement of the implantable device 1200 relative to the tissue in which it is injected. In various embodiments, the entire implantable device 1200 is injected into tissue, and thus the arms 1260 that extend from the anchoring portion 1210 may interface with the tissue to further retain and secure the implantable device 1200 in place. In various embodiments, a similar configuration may be implemented along the immersible portion 1220. That is, instead of or in addition to the auxiliary retention features extending from the anchoring portion, the implantable device may also include a plurality of wings or other features that are circumferentially distributed around a lumen of the immersible portion and that extend radially outward from the immersible portion 1220 of the device 1200. These wings may, as mentioned above, prevent migration (e.g., rotation, etc.) of the implantable device.

Figure 13:
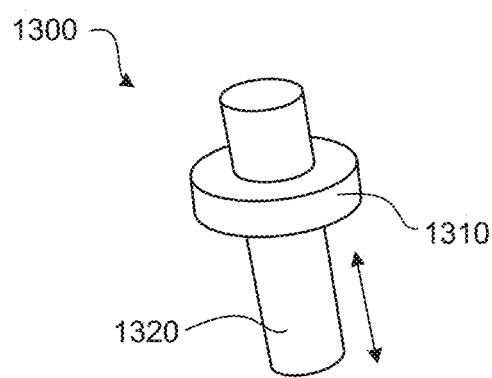
FIGS. 13 and 14 illustrate substrates and/or immersible portions of implantable devices that are detachably coupled to respective anchoring portions, according to various embodiments.
Figure 14:
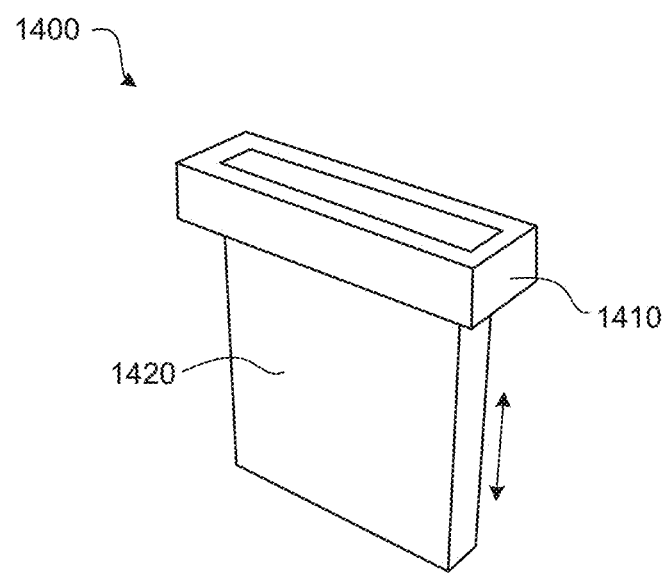
Figure 15:
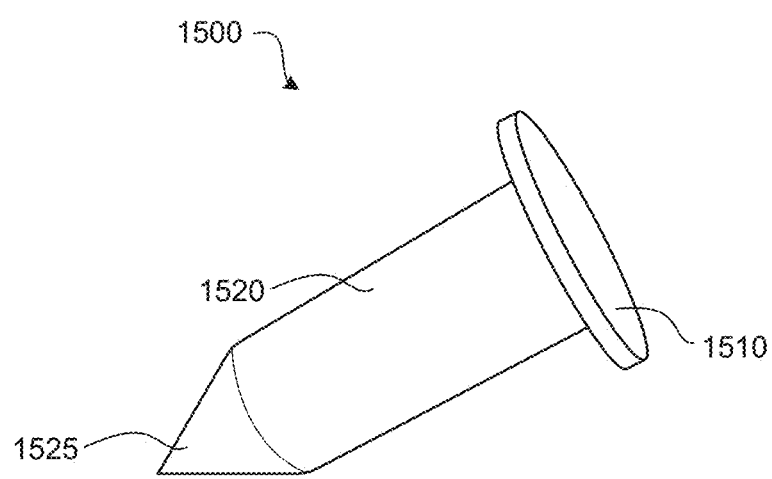
FIG. 15 illustrates an immersible portion of an implantable device that includes a pointed tip to facilitate insertion of the implantable device through tissue, according to various embodiments.

In various embodiments, and with reference to FIG. 13, the implantable device 1300 includes an immersible portion 1320, or at least a substrate of the immersible portion 1320, that is detachably coupled to the anchoring portion 1310. That is, the anchoring portion 1320 may form a dock or other base structure that is attached/anchored to tissue. The anchoring portion 1320 may define an aperture through which the immersible portion 1320 may be inserted (and subsequently extracted, according to various embodiments). Thus, the immersible portion 1320 and/or the substrate contained therein may be removed, replaced, exchanged, and/or regenerated. FIG. 14 shows an embodiment similar to FIG. 13, but with the implantable device 1400 having a rectangular anchoring portion/dock 1410 and a corresponding rectangular immersible portion 1420. In various embodiments, and with reference to FIG. 15, the implantable device comprises an immersible portion 1520 extending from the anchoring portion 1510, wherein the immersible portion 1520 includes the substrate and wherein the immersible portion 1520 has a pointed tip 1525 that is configured to facilitate insertion of the implantable device 1500 through tissue.

Figure 16A:
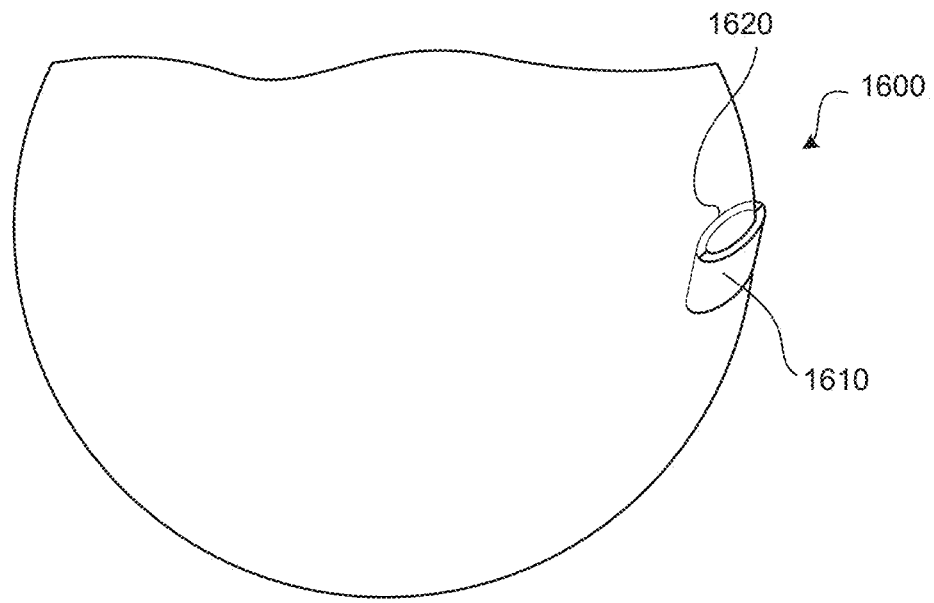
FIGS. 16A and 16B illustrate views of an implantable device that has the form of a loop band configured to be installed in a transcleral position in the eye, according to various embodiments.
Figure 16B:
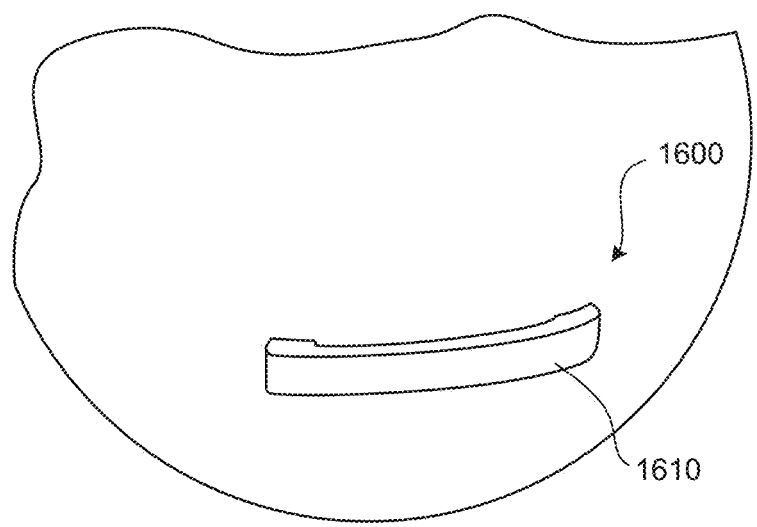

In various embodiments, and with reference to FIGS. 16A and 16B, the implantable device 1600 may comprise a loop band configured to be installed in transcleral position of the eye, wherein a first section 1620 of the loop band is disposed intraocular and a second section 1610 of the loop band is disposed extraocular. In various embodiments, the implantable device 1600 may be made from the substrate and may be formed into a tube or ribbon shape, may be placed through two sclerotomies, with half (e.g., the immersible portion 1620) being intraocular and the other half (e.g., the anchoring portion 1610) being extraocular. In such a configuration, the implantable device 1600 may be rotated (e.g., manually) by grasping the extraocular portion 1610 and rotating. Further, as described in greater detail below pertaining to regeneration, a laser or other regenerating light source could easily be applied to the extraocular portion. If the substrate includes hollow fibers, additional material (drug, perfluorcarbon, steroid, etc) could be injected into the lumen or the extraocular portion.

Figure 17A:
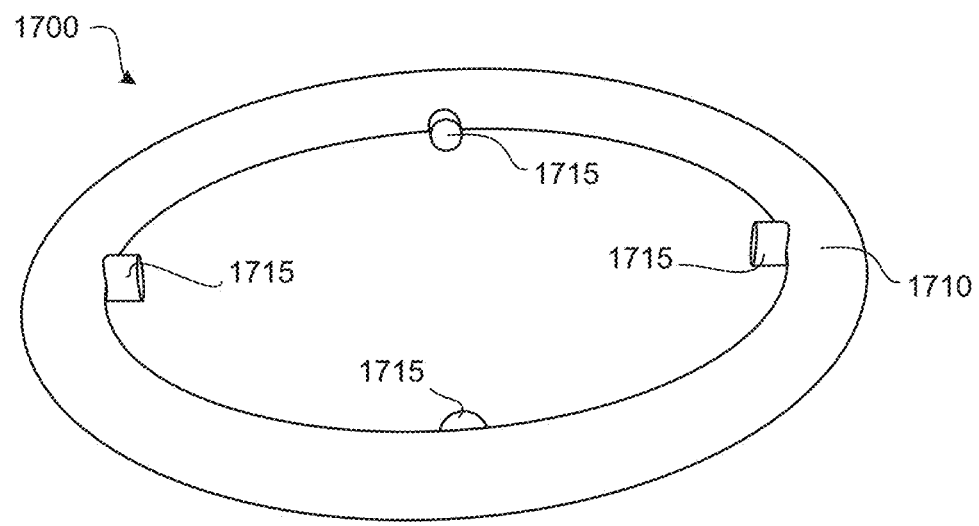
FIGS. 17A and 17B illustrate embodiments of the implantable device having a tubular ring body that are configured to be positioned either externally or internally around the pupil of the eye, according to various embodiments.
Figure 17B:
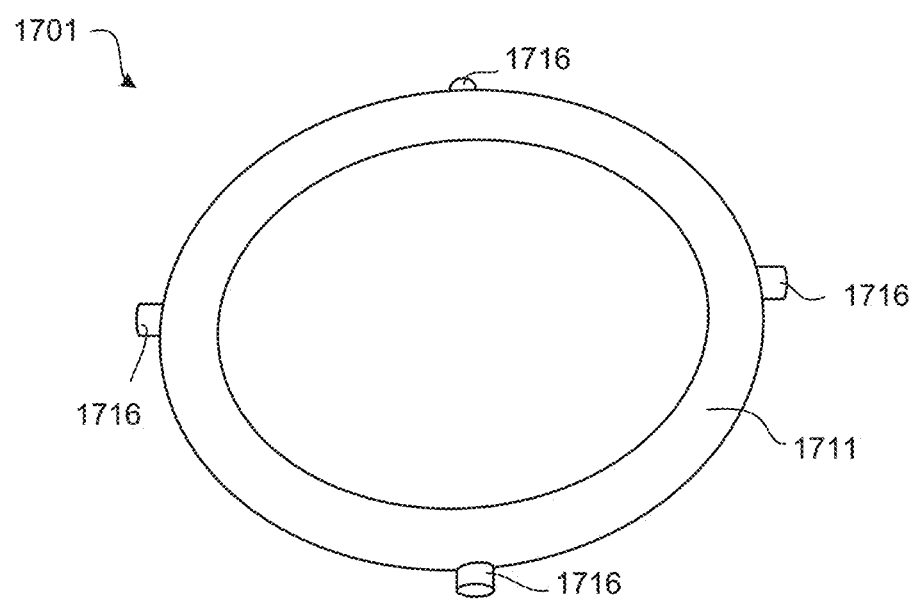

In various embodiments, and with reference to FIGS. 17A and 17B, the anchoring portion of the implantable device 1700 has a tubular ring 1710 formation that is configured to be disposed generally about a pupil of the eye. In such an embodiments, the substrate may be disposed within the tubular ring 1710. In various embodiments, and with specific reference to FIG. 17A, the tubular ring 1710 comprises one or more ports 1715 that extend radially inward, relative to a ring-shape of the tubular ring, such that the tubular ring is configured to be implanted outside a sclera with the one or more ports extending into and through the sclera. In various embodiments, and with specific reference to FIG. 17B, the implantable device 1701 may have a tubular ring 1711 that is configured to be disposed generally about a pupil of the eye. In such an embodiments, the substrate may be disposed within the tubular ring 1711. In various embodiments, and with specific reference to FIG. 17B, the tubular ring 1711 comprises one or more ports 1716 that extend radially outward, relative to a ring-shape of the tubular ring, such that the tubular ring 1711 is configured to be implanted internally (e.g., on a pars plana of the eye).

Figure 18:
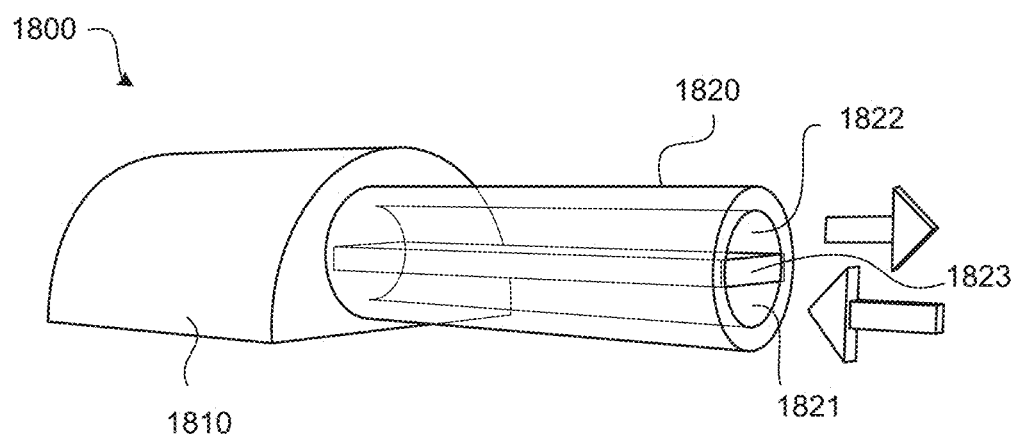
FIG. 18 illustrates an implantable device having a dual lumen configuration, according to various embodiments.
Figure 19:
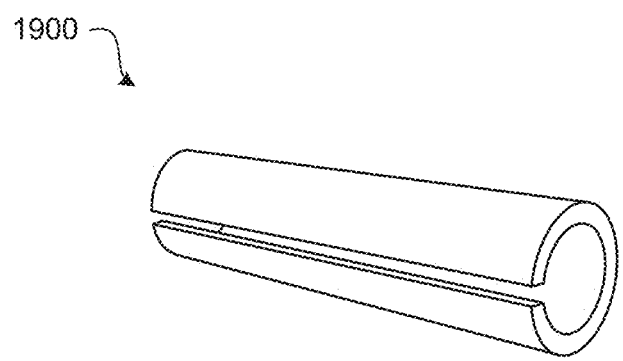
FIG. 19 illustrates a cuff configured to fit around, for example, an optic nerve of a patient, according to various embodiments.

In various embodiments, and with reference to FIG. 18, the implantable device 1800 includes an immersible portion 1820 that extends from an anchoring portion 1810, with the immersible portion 1820 having a dual lumen configuration. That is, the immersible portion 1820 may include a first lumen 1821 and a second lumen 1822, wherein fluid (e.g., vitreous fluid) is configured to flow to the substrate via the first lumen 1821 and fluid is configured to flow from the substrate via the second lumen 1822. In various embodiments, the immersible portion 1820 may include a divider 1823 that extends along the length of the immersible portion 1820 to divide the main body of the immersible portion 1820 into the two lumens 1821, 1822. The anchoring portion 1810 may house or may be formed of the substrate. Alternatively, a portion of the immersible portion 1820 may house or may be formed of the substrate. For example, the divider 1823, or at least a portion thereof, may be the substrate the captures the target molecule. In various embodiments, device 1800 is a glaucoma drainage device. In various embodiments, and with reference to FIG. 19, the implantable device 1900 may include a substrate that has the form of a cuff to be inserted around an optic nerve for treating diseases such as glaucoma, optic neuritis, ischemic optic neuropathies, etc. In such embodiments, the cuff may have a slit/opening to allow the cuff to be installed around the optic nerve.

Figure 20A:
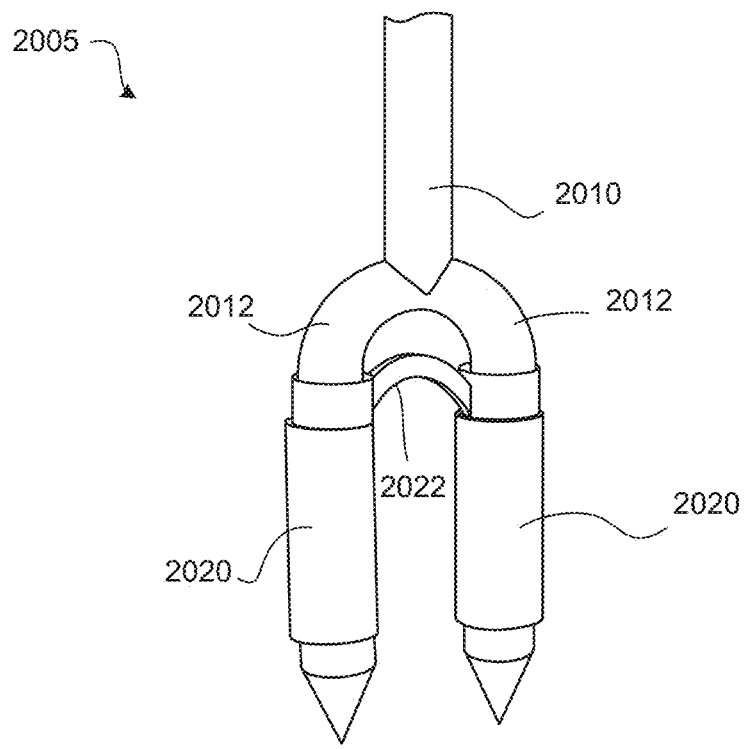
FIGS. 20A and 20B illustrate an implanting system that includes a multi-pronged injector and a plurality of hollow chambers that may be implanted into tissue, according to various embodiments.
Figure 20B:
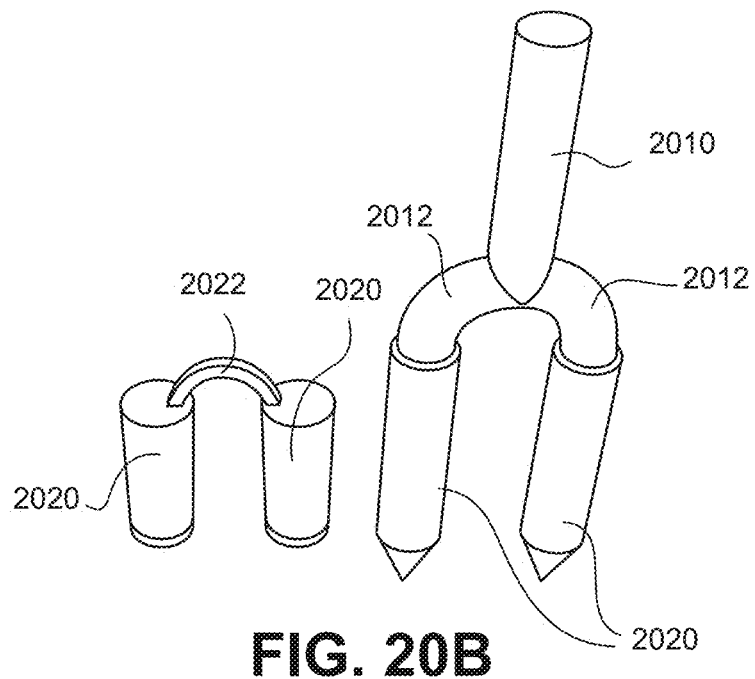

In various embodiments, and with reference to FIGS. 20A and 20B, an implanting system 2005 for treating an ocular disorder is disclosed. The implanting system 2005 may include an injector 2010 that has a plurality of prongs 2012 and a plurality of hollow chambers 2020 that are configured to be loaded onto the plurality of prongs 2012, respectively. That is, each chamber of the plurality of chambers 2020 may be configured to be loaded onto a respective one of the plurality of prongs 2012 of the injector 2010 in a pre-installed state and to be deployed from the respective one of the plurality of prongs 2012 into tissue in an installed state. In various embodiments, the injector is a trocar of sorts that includes pointed tips on each of the prongs to enable insertion of the hollow chambers 2020 into tissue. In various embodiments, the plurality of hollow chambers 2020 may include a tether that extends between the chambers to retain the chambers together. The tether 2022 may facilitate retention of the hollow chambers 2020 within tissue. That is, the tether 2022 may be an anchoring feature. The tether 2022 may remain extraocular, and energy from a regeneration energy source may be directed at the tether to regenerate the substrate, as described in greater detail below. The hollow chambers 2020 may house or may be formed of the substrate material.

In some embodiments, the adsorptive property of the substrate of the implantable device is capable of being regenerated in situ. As used herein, the phrase "capable of being regenerated in situ" indicates that the device is configured such that at least some of the target molecule captured in (or on) the substrate of the device can be released or expelled from the device in a modified form without the need to remove the device from the subject, so that an additional amount of the target molecule can be captured by the device without implanting a second device in the subject. For example, in one embodiment the device can be regenerated by absorbing energy (e.g., heat) from a source external to the subject. In such an embodiment, the absorbed heat modifies the target molecule (e.g., denatures a protein) such that in its modified form it is characterized by a modified biological activity (e.g., a reduced level of its original biological activity, a different biological activity, or no biological activity). As one example, in one embodiment, the device is capable of adsorbing and/or absorbing VEGF and, after exposure to a thermal source (e.g., a thermal laser such as an argon laser, a diode, a femtosecond laser, a neodymium-doped yttrium aluminum garnet (Nd:Yag) laser, a photodynamic laser, a photodisruptive laser, or a combination thereof), is capable of releasing denatured VEGF. In another embodiment, the device is regenerated by applying cryotherapy to the device. Without wishing to be bound by theory, in such an embodiment it is believed that the decrease or increase in temperature of the adherent proteins causes denaturation and inactivation of biological activity. Alternatively, electrical current or electromagnetic energy may be passed through the device to cause protein denaturation. Further, changing the local pH, desiccation, radiation, or doping with elements may all be used to interfere or degrade the biological function of the target protein.

Photodynamic therapy, or other light-sensitive materials, may be used to inactivate the adherent proteins. Additionally, the process of laser induced surface plasmon resonance such as with quantum dots may be used to generate a local thermal reaction. Accordingly, in some embodiments, the device has a higher affinity for the target molecule compared to its corresponding modified target molecule (e.g., its thermally denatured target molecule). In some embodiments, the modified target molecule comprises one or more degradation products of the target molecule. Further, the substrate may be treated with fluorophores or other chemical moieties such that the amount of protein adsorbed to the surface is visible by color change, perceptible by indirect ophthalmoscopy, direct visualization, or using confocal scanning laser technology, filters, or other means. The implant may be translucent or clear, allowing the practitioner to laser all surfaces by means of adjusting the laser's focal point. Further, solid implants may be capable of rotating along the major axis, allowing the practitioner to visualize and apply laser energy to the surface in its entirety.

In some embodiments, a device as described herein may comprise one or more energy emitters such as quantum dots configured to emit a sufficient amount of at least one of an electromagnetic stimulus, an electrical stimulus, an ultrasonic stimulus, and a thermal stimulus to ablate or induce ablation of the adherent target molecule in order to facilitate adsorption or dissolution of target molecules. One or more energy emitters may be housed within an internal lumen of a device in accordance with the present disclosure. Example energy emitters include, but are not limited to quantum dots, electric circuits, electrical conductors, electrodes (e.g., nano- and micro-electrodes, patterned-electrodes, electrode arrays (e.g., multi-electrode arrays, micro-fabricated multi-electrode arrays, patterned-electrode arrays, or the like), electrocautery electrodes, cavity resonators, conducting traces, ceramic patterned electrodes, electro-mechanical components, lasers, laser diodes, light-emitting diodes (e.g., organic light-emitting diodes, polymer light-emitting diodes, polymer phosphorescent light-emitting diodes, microcavity light-emitting diodes, high-efficiency UV light-emitting diodes, or the like), arc flashlamps, incandescent emitters, transducers, heat sources, continuous wave bulbs, ultrasound emitting elements, ultrasonic transducers, thermal energy emitting elements, and the like.

Energy emitters forming part of the implantable device, can take a variety of forms, configurations, and geometrical patterns including for example, but not limited to, a one-, two-, or three-dimensional arrays, a pattern comprising concentric geometrical shapes, a pattern comprising rectangles, squares, circles, triangles, polygons, any regular or irregular shapes, or the like, or any combination thereof. One or more of the energy emitters can have a peak emission wavelength in the x-ray, ultraviolet, visible, infrared, near infrared, terahertz, microwave, or radio frequency spectrum. In various embodiments, the substrate may include one or more energy emitters embedded into, integrally within, or impregnated onto the substrate, and the energy emitters may, in response to uptake of energy from a regeneration energy source, facilitate denaturing of the target molecule captured by the substrate. The energy emitters may comprise gold nanoparticles, gold particles, perfluorocarbons, and/or aqueous solutions with wavelength specific hues, among other materials.

In various embodiments, as described above in conjunction with various figures, the implantable device may define a port or a window. The laser or other regenerating energy may be directly applied to the implantable device via the port or window. The substrate may alternatively be removed, replaced, or exchanged via the port. In various embodiments, the energy emitters (also referred to as the thermal amplification material) may be removed, replaced, and/or exchanged via the port.

In various embodiments, the substrate may be coated with one or more materials that are configured to further facilitate capture of the target molecule(s). That is, a coating applied to the substrate may improve the ability of the substrate to capture and retain target molecules to be subsequently denatured via regeneration. The coating may include materials comprising gold, zinc, and/or calcium, among others.

One embodiment of a method of the present disclosure is depicted in FIG. 1. A device of the present disclosure 100 is implanted in the eye 10 of the subject. In some embodiments, the device is capable of being implanted through an incision. In some embodiments, the device is capable of being implanted by injection. In some embodiments, the device is capable of being implanted in and/or through (e.g., is in contact with) tissue of an eye, for example in or through the pars plana. In some embodiments, the device 100 is implanted through (e.g., is in contact with) one or more of: the sclera 16, the choroid 14, and/or the retina 12.

In some embodiments at least a portion of the implantable device (e.g., immersed or immersible portion 120, 220) has a porous or microporous surface. In some embodiments, the surface of at least a portion of device has an average pore diameter of less than 1 mm, for example about 1 mm, about 0.95 mm, about 0.9 mm, about 0.85 mm, about 0.8 mm, about 0.75 mm, about 0.7 mm, about 0.65 mm, about 0.6 mm, about 0.55 about 0.5 mm, about 0.45 mm, about 0.4 mm, about 0.35 mm, about 0.3 mm, about 0.25 mm, about 0.2 mm, about 0.15 mm, about 0.1 mm, about 0.05 mm, or less than about 0.05 mm.

In one embodiment, the present disclosure provides a method of treating an ocular disorder in a subject, the method comprising implanting into an eye of the subject, and in contact with fluid of the eye, a device as disclosed herein; and thereafter capturing the target molecule from the fluid. In one embodiment, the eye has previously undergone vitrectomy or other ocular surgery.

In some embodiments, the method further comprises, after capturing the target molecule from fluid of the eye, regenerating the adsorptive properties of the device in situ.

In some embodiments, the step of regenerating the device in situ comprises exposing the device to an energy source, such as a laser, for example from a laser indirect opthalmoscope. In some embodiments, the method further comprises, after regenerating the device in situ, capturing an additional amount of the target molecule from fluid of the eye.

In some embodiments, the implanted device is left in place for a period of time sufficient to reduce or alleviate one or more symptoms of the ocular disorder, for example about one month, about 2 months, about 3 months, about 4 months, about 5 months, about 6 months, about 7 months, about 8 months, about 9 months, about 10 months, about 11 months, about 12 months, or more than 12 months. In some embodiments, the device is regenerated at least once, at least twice, at least 3 times, at least 4 times, at least 5 times, at least 6 times, at least 7 times, at least 8 times, at least 9 times, at least 10 at least 11 times, at least 12 times, or more than 12 times before removal from the subject. In an alternative embodiment, the device is removed after a period of time sufficient for it to become saturated with the target molecule, for example after about 1 about 2 weeks, about 3 weeks, about 4 weeks, about 5 weeks, about 6 weeks, about 7 weeks, about 8 weeks, about 9 weeks, about 10 weeks, about 11 weeks, about 12 about 4 months, about 5 months, about 6 months, about 7 months, about 8 about 9 months, about 10 months, about 11 months, about 12 months.

In some embodiments, a method of treating an ocular disorder in a subject on intraocular injection therapy comprises, consists essentially of, or consists of optionally identifying the subject as being on intraocular injection therapy; implanting into an eye of the subject, and in contact with fluid of the eye, a device comprising a substrate capable of capturing a target molecule present in fluid of the eye; capturing the target molecule from the fluid; and optionally after capturing the target molecule from the fluid, regenerating the device in situ. In some embodiments, the intraocular injection therapy comprises administration of ranibizumab, bevacizumab and/or pegaptanib. In some embodiments, the target molecule is an angiogenic compound, optionally VEGF. In some embodiments, the optional step of regenerating the device in situ comprises contacting the device with a thermal laser to denature and/or decompose at least a portion of the captured target molecule.

In some embodiments, a method of the present disclosure comprises replacing existing intraocular injection therapeutic regimen with a second treatment regimen comprising, consisting essentially of, or consisting of implanting into an eye of the subject, and in contact with fluid of the eye, a device comprising a substrate capable of capturing a target molecule present in fluid of the eye; capturing the target molecule from the fluid; and optionally after capturing the target molecule from the fluid, regenerating the device in situ. In some embodiments, the existing intraocular injection therapy is discontinued before, concomitantly with, or after implanting the device into the eye of the subject. In some embodiments, the target molecule is an angiogenic compound, optionally VEGF. In some embodiments, the optional step of regenerating the device in situ comprises contacting the device with a thermal laser to denature and/or decompose at least a portion of the captured target molecule.

EXAMPLES

Example 1: Acute Model

Twenty white cross rabbits are divided into three groups: control, active implant (bioceramic), and inactive implant (standard plastic). Baseline photographs, electroretinograms, and intravitreal VEGF levels are performed on all subjects. The active and inactive implant groups undergo surgery and two weeks later all three groups receive in the right eye a standardized dose of VEGF in a polymer pellet which has a sustained release profile sufficient to induce vasoproliferation in a reliable and repeatable manner. Repeat examinations, fundus photography, fluorescein angiography, and intravitreal VEGF sampling are performed at 24 hrs, 48 hrs, 4 days, 7 days, 14 days, 21 days, and 28 days post-surgery. Prior to harvesting the eyes for histological examination, final electroretinograms are performed. Subsequent grading of observed neovascularization is performed by a masked observer using the system described by Ozaki et al., "Intravitreal sustained release of VEGF causes retinal neovascularization in rabbits and breakdown of the blood-retinal barrier in rabbits and primates," Exp. Eye Res., vol. 64(4), pages 505-17 (1997).

Example 2: Chronic Model

A subset of subjects from Example 1 are observed for an additional 9 months in order to determine long-term stability and biocompatibility of the implanted device. Exams, fundus photography, angiography, electroretinography and VEGF sampling are performed each month.

Example 3: Regeneration of Implantable Devices by Thermal Laser

Bioceramic discs composed of porous hydroxyapatite were soaked overnight in 50 µL of deionized water containing 50 ng of VEGF, each in a separate well of a 96-well plate. The discs soaked for 24 hours with periodic gentle agitation, after which the excess solution was removed. The amount of VEGF in this solution was determined using a human VEGF ELISA kit. The estimated amount of VEGF loaded into the implant was determined by subtracting the amount in the solution from the loading amount. The hydroxyapatite discs adsorbed an average of 14 ng of VEGF, compared to less than 1 ng for a control group consisting of plastic beads ($p<0.05$).

Next, half of the hydroxyapatite discs were exposed to argon laser (240 mW power, 0.2 ms duration, 100 spots over 2 minutes), sufficient to induce a rise in the surface temperature of the discs of 8° C., as measured by an infrared thermometer. The other half of the pellets were exposed to light for 2 minutes, without exposure to laser and without surface temperature change. All the pellets were then placed in separate wells of another 96-well plate and allowed to soak 48 hours in Dl water with gentle agitation. The amount of VEGF released from each pellet was then measured again using the VEGF ELISA kit. The discs exposed to light released about 30% of the initial loading dose of VEGF, compared to about 5% in the lasered group ($p<0.05$). These data demonstrate that the bioceramic material can sequester VEGF, which can be further inactivated by thermal laser.

Example 4: Adsorption of Complement Factor D by PAN Fibers

An experiment was conducted to assess adsorption of complement Factor D by PAN fibers as compared to polypropylene capillaries according to the below protocol.

Hydrate and Equilibrate PAN and polypropylene fibers
  Cut PAN fibers into small fragments <4 mm in length[1]
  Measure 3 samples each of 50 mg PAN and polypropylene fibers in separate eppendorf tubes [45 mg max amount used by Pascual and Schifferti[1] however they had a slightly lower amount of Complement Factor D in their samples]
  Add 675 ul Elisa wash/dilution buffer (W/d b) into each tube [since Elisa is going to be used to analyze the samples]
  Mix well by tapping
  Incubate at 37 degree C. for 1 hour[1] [alternatively could incubate at room temperature for 12 hours]
  Wash twice with 675 ul W/d d at room temp
  Suspend in 675 ul W/d d at room temp
Prepare samples:
Negative Control (NC): 3 samples
  Tube 1: total volume 675 ml [20 ng/ml CF-D concentration, maximal concentration detected by Elisa kit]
  672 ul W/d b
  13.2 ng Complement Factor D (CF-D) (3 ul of 4.4 ng/ul CF-D standard) [3 ul=12.5 ng used by Pascual and Schifferti[1]]
  Mix well by tapping
  Tube 2: total volume 675 ml
  672 ul W/d b
  13.2 ng CF-D (3 ul of 4.4 ng/ul CF-D standard)
  Mix well by tapping
  Tube 3: total volume 675 ml
  672 ul W/d b
  13.2 ng CF-D (3 ul of 4.4 ng/ul CF-D standard)
  Mix well by tapping
Experiment (E): 3 samples
  Tube 1: total volume 675 ml [20 ng/ml CF-D concentration, maximal concentration detected by Elisa kit]
  672 ul W/d b (room temp solution)
  13.2 ng CF-D (3 ul of 4.4 ng/ul CF-D standard) [3 ul=12.5 ng used by Pascual and Schifferti1]
  Mix well by tapping
  Add 50 mg hydrated and equilibrated PAN membranes
  Mix well by tapping
  Tube 2: total volume 675 ml
  672 ul W/d b (room temp solution)
  13.2 ng CF-D (3 ul of 4.4 ng/ul CF-D standard)
  Mix well by tapping
  Add 50 mg hydrated and equilibrated polypropylene membranes
  Mix well by tapping
  Tube 3: total volume 675 ml
  672 ul W/d b (room temp solution)
  13.2 ng CF-D (3 ul of 4.4 ng/ul CF-D standard)
  Mix well by tapping
  Add 50 mg hydrated and equilibrated polypropylene membranes
  Mix well by tapping
Incubate samples for 1 hour at 37 degree C. [alternately could incubate at room temperature for 12 hours; then it would not be needed to bring samples to room temperature for analysis after incubation]
Prepare serial dilution for calibration curve according to serial dilution protocol per Hycult Biotech CFD Elisa Kit manual (p.7) with the following concentrations:
  Tube 1: 20 ng/ml
  Tube 2: 13/3 ng/ml
  Tube 3: 8.9 ng/ml
  Tube 4: 5.9 ng/ml
  Tube 6: 2.6 ng/ml
  Tube 7: 1.8 ng/ml
  Tube 8: 0 ng/ml (blank; W/D b only)

Take samples out of 37 degree incubator, mix samples well by tapping, and transfer 375 ul out of each sample tube into a new eppendorf tube at room temperature to be used for Elisa analysis Keep to-be-analyzed samples at room temperature for 1 hour, since room temperature is required for Elisa analysis Perform ELISA on the prepared samples (3×100 ug wells per sample) following the protocol per Hycult Biotech CFD Elisa Kit manual (p.9)

Well Lay-Out:

| T1 | T1 | NC1 | NC1 | NC1 | NC2 |
| T2 | T2 | NC2 | NC2 | NC3 | NC3 |
| T3 | T3 | NC3 | E1 | E1 | E1 |
| T4 | T4 | E2 | E2 | E2 | E3 |
| T5 | T5 | E3 | E3 | S1 | S1 |
| T6 | T6 | S1 | S2 | S2 | S2 |
| T7 | T7 | S3 | S3 | S3 | empty |
| T8 | T8 | empty | empty | empty | empty |

Measure absorbance at 450 nm

REFERENCE

1. Pascual, M. and J. A. Schifferti (1993). "Adsorption of complement factor D by polyacrylonitrile dialysis membranes." *Kidney Int* 43(4): 903-911.

Figure 3:
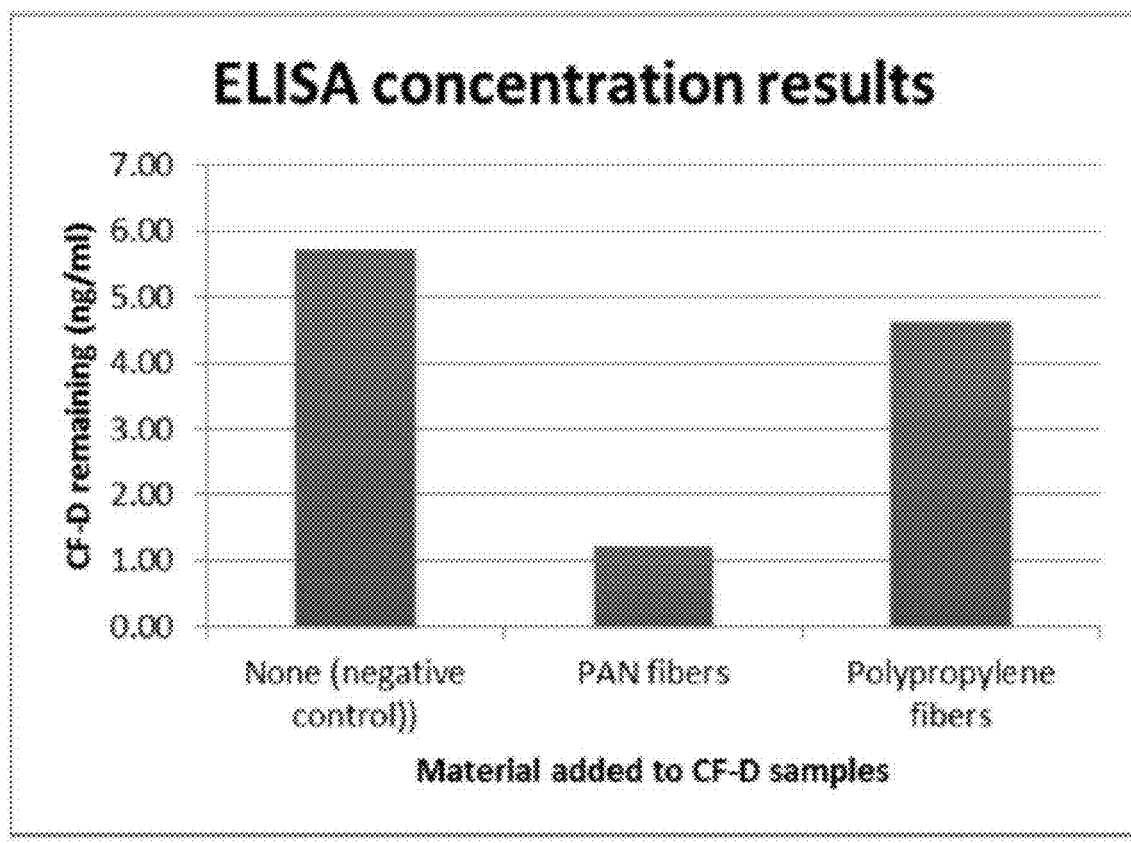
FIG. 3 shows ELISA concentration results when complement Factor D (CFD) was incubated in vials containing polyacrylonitrile (PAN) dialysis fibers, a control containing polypropylene fibers, and a negative control. The solution remaining was then examined using spectrophotometry. The results indicate that PAN is taken up in very high amounts by the PAN membranes compared to the controls, according to various embodiments.
Figure 4:
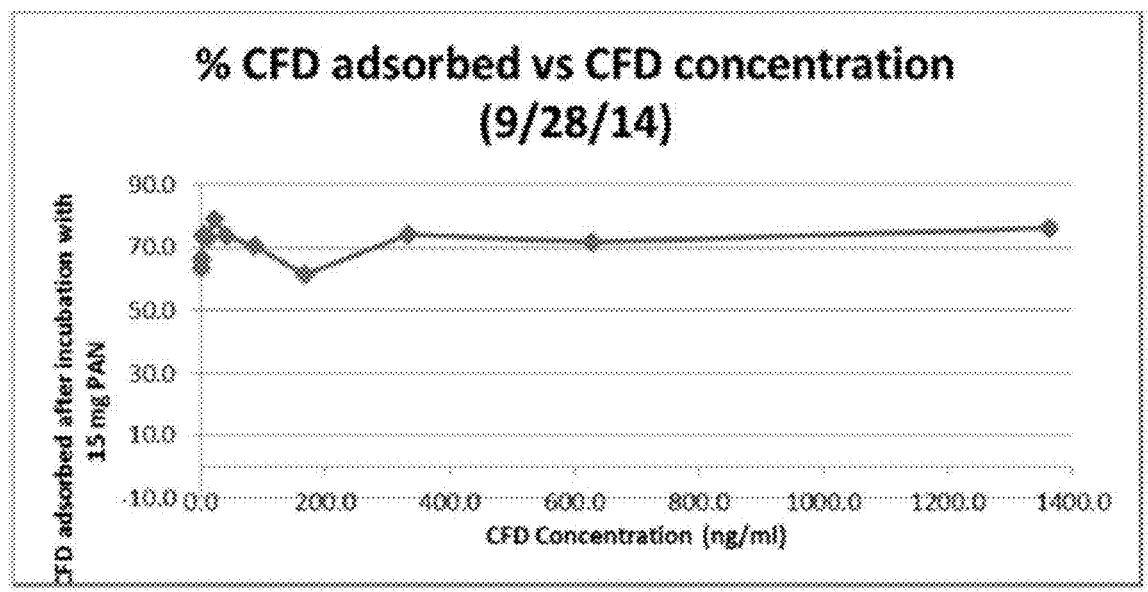
FIG. 4. demonstrates that when CFD is incubated with PAN membranes, the protein is taken up by the membrane well, and even at very high concentrations does not show saturation, indicating that the membrane can adsorb very high levels of the protein, according to various embodiments.

Results are shown in FIGS. 3 and 4. Overall, these experiments demonstrate that a type of membrane (polyacrylonitrile) will adsorb high amounts of a protein called Complement Factor D (CFD), which is thought to be a major therapeutic target in dry macular degeneration.

Example 5: In Vitro VEGF Adsorption

An In Vitro Adsorption Experiment was Conducted According to the Following Protocol:

Three groups were tested: hydroxyapatite implant, acrylic bead, and control. A total of nine wells were used, three per group, and the experiment run three times. Each well contained a standard concentration of VEGF 400 pg/mL. The implants and beads were placed in the respective wells, and all wells kept at 4 degrees Celsius for 24 hours. The hydroxyapatite implants and the acrylic beads were then removed from solution, washed with saline, and the amount of VEGF removed by washing measured and added to the total VEGF measured in solution. There was a statistically significant difference between the hydroxyapatite group and the acrylic bead and control groups, but not between the acrylic bead and control group ($p<0.05$).

For the hydroxyapatite group, a mean of 64 pg/mL of VEGF remained in solution, compared to 359 pg/ML and 369 pg/mL for the acrylic bead and control groups respectively. The amount of VEGF adsorbed is obtained by subtracting the VEGF remaining in the solution from the total initial concentration. The HA implant adsorbed on average 336 pg/mL, compared to 41 pg/mL for the acrylic bead group and 31 pg/mL for the control group.

Figure 5:
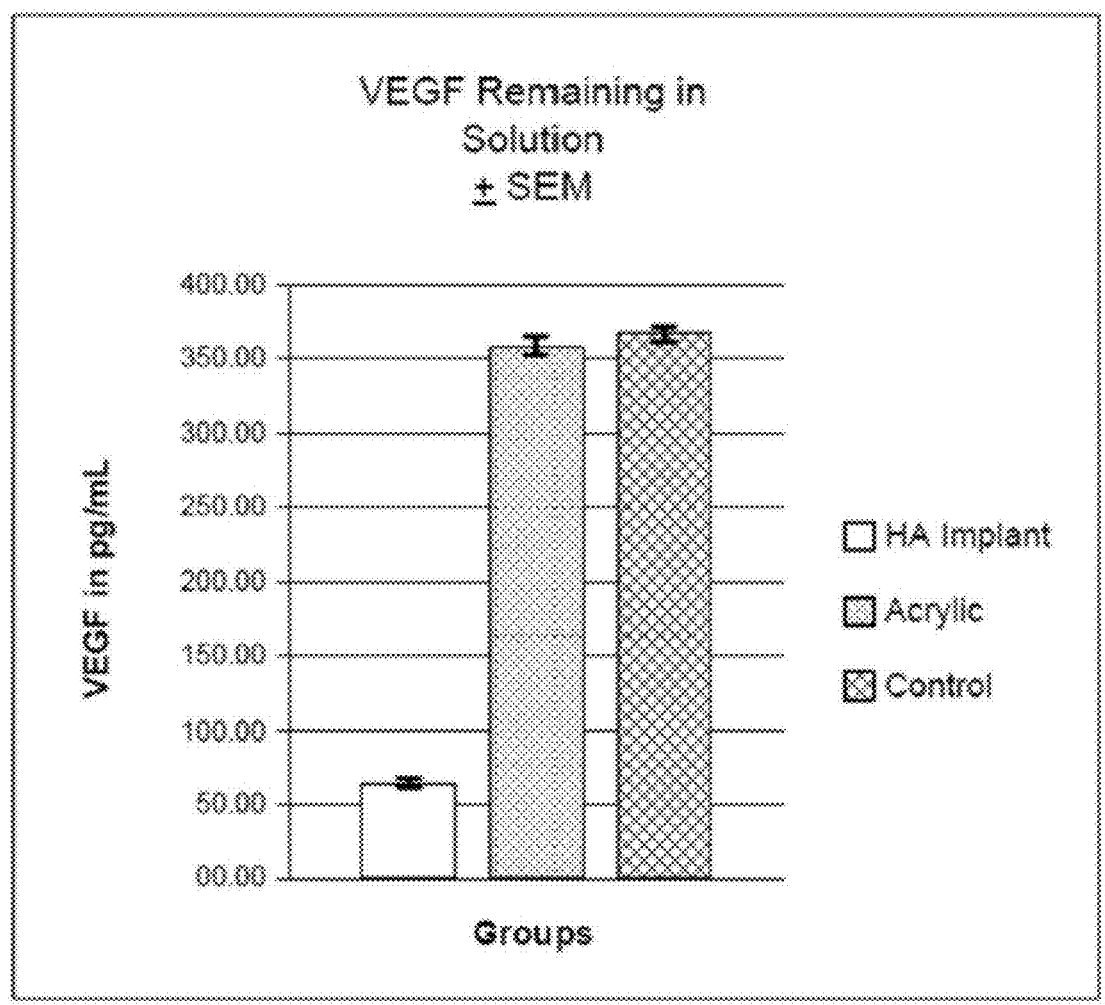
FIG. 5 shows results of an in vitro VEGF adsorption assays and in particular that VEGF levels remaining in solution were significantly lower in the HA implant group, indicating that VEGF is strongly adsorbed by the hydroxyapatite implant, according to various embodiments.

Results are shown in FIG. 5 and demonstrate that VEGF levels remaining in solution were significantly lower in the HA implant group, indicating that VEGF is adsorbed by the hydroxyapatite implant.

Any of the embodiments contemplated herein can be used to adsorb complement, proteins, and other target molecules in the cerebrospinal fluid and the like associated with Alzheimer's disease, multiple sclerosis, amyotropic lateral sclerosis, Parkinson's disease, peripheral neuropathy, major depression, or similar diseases. Any of the embodiments described could also be implanted via a transvitreal approach for subretinal delivery, transvitreal approach for delivery into the optic nerve sheath, transcranial approach for delivery to an intracranial vessel, traditional Pars plana vitrectomy (PPV) approach for subretinal implantation, posterior approach after laser pre-treatment, or similar implantation modes.

In some embodiments, the implantable device is further capable of delivering a drug to the subject. In some embodiments, the drug is an anti-VEGF compound such as ranibizumab, bevacizumab or pegaptanib, or a steroid. The drug may be loaded into the substrate by forced pressure or vacuum techniques, filling the porous cavities of the device with the intended therapeutic agent, whether solid, powder, liquid, or gas. In various embodiments, the implantable device may include an adjustable distal port for drug delivery. The adjustable distal port may be actuated using heat or other energy source. In various embodiments, drug delivery may be facilitated by the substrate regeneration process described above. That is, directed laser/thermal energy to the substrate may cause an increase in substrate temperature, which denatures the adherent molecules (e.g. proteins) and concurrently causes a drug delivery port of the implantable device to expand to deliver a dosage of drug (or to increase the continuous dosage of drug). In various embodiments, the substrate may be loaded with a drug in gel form, which allows slow and sustained drug delivery over a period of time. In various embodiments, a woven mesh structure may be disposed extraocular, and the void spaces of the mesh may be filled with drugs/steroids in an extended release form. Once only the mesh is visible, a practitioner may know that the drug has been delivered.

In various embodiments, portions of the implantable device may be made from a shape memory polymer to allow it to assume a desired shape/size upon installation, thus improving the retention and fit of the implantable device. In various embodiments, a suture, wire, or filament may be used to help install the implantable device (e.g., similar to a guide wire), and/or retain the implantable device in place. Additionally, such a suture, wire, or filament may be used to pass energy (heat, electricity, etc.) from a surface of the eye to the substrate/lumen that is immersed within the eye. In various embodiments, a sheet for subretinal/preretinal implantation may be utilized, and the sheet may be porous for oxygen/nutrient exchange. This sheet may be thin and may be used as a complement blocking scaffold for RPE/stem cell transplants.

Benefits, other advantages, and solutions to problems have been described herein with regard to specific embodiments. Furthermore, the connecting lines shown in the various figures contained herein are intended to represent exemplary functional relationships and/or physical couplings between the various elements. It should be noted that many alternative or additional functional relationships or physical connections may be present in a practical system. However, the benefits, advantages, solutions to problems, and any elements that may cause any benefit, advantage, or solution to occur or become more pronounced are not to be construed as critical, required, or essential features or elements of the disclosure.

The scope of the disclosure is accordingly to be limited by nothing other than the appended claims, in which reference to an element in the singular is not intended to mean "one and only one" unless explicitly so stated, but rather "one or more." It is to be understood that unless specifically stated otherwise, references to "a," "an," and/or "the" may include one or more than one and that reference to an item in the singular may also include the item in the plural. All ranges and ratio limits disclosed herein may be combined.

Moreover, where a phrase similar to "at least one of A, B, or C" is used in the claims, it is intended that the phrase be interpreted to mean that A alone may be present in an embodiment, B alone may be present in an embodiment, C alone may be present in an embodiment, or that any combination of the elements A, B and C may be present in a single embodiment; for example, A and B, A and C, B and C, or A and B and C. Different cross-hatching is used throughout the figures to denote different parts but not necessarily to denote the same or different materials.

The steps recited in any of the method or process descriptions may be executed in any order and are not necessarily limited to the order presented. Furthermore, any reference to singular includes plural embodiments, and any reference to more than one component or step may include a singular embodiment or step. Elements and steps in the figures are illustrated for simplicity and clarity and have not necessarily been rendered according to any particular sequence. For example, steps that may be performed concurrently or in different order are illustrated in the figures to help to improve understanding of embodiments of the present disclosure.

Any reference to attached, fixed, connected or the like may include permanent, removable, temporary, partial, full and/or any other possible attachment option. Additionally, any reference to without contact (or similar phrases) may also include reduced contact or minimal contact. Surface shading lines may be used throughout the figures to denote different parts or areas but not necessarily to denote the same or different materials. In some cases, reference coordinates may be specific to each figure.

Systems, methods and apparatus are provided herein. In the detailed description herein, references to "one embodiment", "an embodiment", "various embodiments", etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described. After reading the description, it will be apparent to one skilled in the relevant art(s) how to implement the disclosure in alternative embodiments.

Furthermore, no element, component, or method step in the present disclosure is intended to be dedicated to the public regardless of whether the element, component, or method step is explicitly recited in the claims. No claim element is intended to invoke 35 U.S.C. 112(f) unless the element is expressly recited using the phrase "means for." As used herein, the terms "comprises", "comprising", or any other variation thereof, are intended to cover a non-exclusive inclusion, such that a process, method, article, or apparatus that comprises a list of elements does not include only those elements but may include other elements not expressly listed or inherent to such process, method, article, or apparatus.

What is claimed is:

1. An implantable device for treatment of an ocular disorder, the implantable device, comprising:
   an anchoring portion configured to secure the implantable device to a tissue of an eye; and
   a substrate coupled to the anchoring portion, wherein the substrate is configured to be disposed in at least one of a vitreous humour and an aqueous humour of the eye, wherein the substrate comprises an affinity for capturing a target molecule.

2. The implantable device of claim 1, wherein the implantable device comprises an immersible portion extending from the anchoring portion, wherein the immersible portion comprises the substrate, wherein the immersible portion also comprises a compressible lumen, wherein in response to blinking or other such action by a patient, the compressible lumen is configured to compress to facilitate fluid flow through the compressible lumen.

3. The implantable device of claim 1, wherein the implantable device comprises an immersible portion extending from the anchoring portion, wherein the immersible portion comprises the substrate, wherein the immersible portion comprises a retention feature configured to prevent inadvertent extraction of the implantable device from the eye.

4. The implantable device of claim 3, wherein the retention features comprises a bulbous ring extending circumferentially around a lumen of the immersible portion.

5. The implantable device of claim 4, wherein the bulbous ring is inflatable.

6. The implantable device of claim 3, wherein the retention feature comprises one or more ridges extending circumferentially around a lumen of the immersible portion.

7. The implantable device of claim 3, wherein the retention feature comprises one or more wings that are circumferentially distributed around a lumen of the immersible portion, wherein the one or more wings extend radially outward from the lumen.

8. The implantable device of claim 1, wherein the substrate is detachably coupled to the anchoring portion.

9. The implantable device of claim 1, wherein the implantable device comprises a loop band configured to be installed in transcleral position of the eye, wherein a first section of the loop band is disposed intraocular and a second section of the loop band is disposed extraocular.

10. The implantable device of claim 1, wherein the implantable device comprises an immersible portion detachably coupled to the anchoring portion, wherein the immersible portion comprises the substrate.

11. The implantable device of claim 1, wherein the implantable device comprises an immersible portion extending from the anchoring portion, wherein the immersible portion comprises a first lumen and a second lumen, wherein fluid is configured to flow to the substrate via the first lumen and fluid is configured to flow from the substrate via the second lumen.

12. The implantable device of claim 1, wherein the anchoring portion comprises a tubular ring configured to be disposed generally about a pupil of the eye, wherein the substrate is disposed within the tubular ring.

13. The implantable device of claim 12, wherein the tubular ring comprises one or more ports that extend radially inward, relative to a ring-shape of the tubular ring, such that the tubular ring is configured to be implanted outside a sclera with the one or more ports extending into and through the sclera.

14. The implantable device of claim 12, wherein the tubular ring comprises one or more ports that extend radially outward, relative to a ring-shape of the tubular ring, such that the tubular ring is configured to be implanted internally on a pars plana of the eye.

15. The implantable device of claim 1, wherein the anchoring portion defines a port, wherein the substrate is configured to be at least one of removed, exchanged, replaced, and regenerated via the port.

16. The implantable device of claim 1, wherein the substrate comprises a plurality of energy emitters, wherein the plurality of energy emitters, in response to uptake of a regeneration energy source, are configured facilitate denaturing of the target molecule captured by the substrate.

17. The implantable device of claim 16, wherein the plurality of energy emitters are at least one of embedded into, integrated within, and impregnated onto a material of the substrate.

18. The implantable device of claim 17, wherein the plurality of energy emitters comprises at least one of gold nanoparticles, gold particles, perfluorocarbons, and aqueous solutions with wavelength specific hues.

\* \* \* \* \*